US006767637B2

(12) United States Patent
Park et al.

(10) Patent No.: US 6,767,637 B2
(45) Date of Patent: Jul. 27, 2004

(54) MICROENCAPSULATION USING ULTRASONIC ATOMIZERS

(75) Inventors: Kinam Park, West Lafayette, IN (US); Yoon Yeo, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 10/392,245

(22) Filed: Mar. 19, 2003

(65) Prior Publication Data

US 2003/0230819 A1 Dec. 18, 2003

Related U.S. Application Data

(63) Continuation-in-part of application No. 10/017,338, filed on Dec. 13, 2001, now Pat. No. 6,599,627.
(60) Provisional application No. 60/365,411, filed on Mar. 19, 2002, provisional application No. 60/254,920, filed on Dec. 13, 2000, and provisional application No. 60/294,263, filed on May 31, 2001.

(51) Int. Cl.[7] .......................... B32B 15/02; B01J 13/02

(52) U.S. Cl. .................... 428/402.21; 264/4.1; 264/4.3; 264/4.33; 427/213.3; 427/213.36; 428/402.2; 428/403

(58) Field of Search ......................... 428/402.2, 402.21, 428/403; 264/4.1, 4.3, 4.33; 427/213.3, 213.36

(56) References Cited

U.S. PATENT DOCUMENTS

| | | | |
|---|---|---|---|
| 3,523,906 A | | 8/1970 | Vrancken et al. |
| 4,389,330 A | | 6/1983 | Tice et al. |
| 5,017,383 A | | 5/1991 | Ozawa et al. |
| 5,019,400 A | | 5/1991 | Gombotz et al. |
| 5,100,669 A | | 3/1992 | Hyon et al. |
| 5,389,379 A | | 2/1995 | Dirix et al. |
| 6,020,004 A | | 2/2000 | Shah |
| 6,077,543 A | | 6/2000 | Gordon et al. |
| 2002/0044976 A1 | | 4/2002 | Gustavsson et al. |

FOREIGN PATENT DOCUMENTS

| | | |
|---|---|---|
| JP | 2001-190943 A2 | 7/2001 |
| WO | WO 01/15799 A1 | 3/2001 |

OTHER PUBLICATIONS

Langer, R. et al., 1976, "Polymers for the sustained release of proteins and other macromolecules" *Nature*, 263: 797–800.

Ogawa, Y., et al., 1988, "A new technique to efficiently entrap leuprolide acetate into microcapsules of polylactic acid or copoly(lactic/glycolic) acid" *Chem Pharm Bull*, 36: 1095–1103.

(List continued on next page.)

*Primary Examiner*—Samuel A. Acquah
(74) *Attorney, Agent, or Firm*—Medicus Associates; James H. Meadows

(57) ABSTRACT

A method for generating a plurality of drug-containing microcapsules employs one or more atomizers to form the microcapsules by the phenomenon of solvent exchange. A plurality of microdroplets of an aqueous solution is contacted with a plurality of microdroplets containing a polymer dissolved in a hydrophilic solvent under conditions whereby the polymer solution envelops the aqueous microdroplet. Exchange of solvent molecules between the aqueous core and its polymer-containing shell deposits the polymer as a membrane around the aqueous core. A preferred atomizer is a coaxial ultrasonic atomizer. Microcapsules can be generated in air as well as when submersed in a collection bath. Desired properties of the microcapsules, e.g., controlled release, can be achieved by providing protective excipients within the aqueous core, providing a hydrophilic polymer capable of undergoing a sol-to-gel transition within the aqueous core, optimizing selection of the polymer solvent, adjusting relative flow rates, and the like.

30 Claims, 9 Drawing Sheets

OTHER PUBLICATIONS

Ogawa, Y., et al., 1988, "In vivo release profiles of leuprolide acetate from microcapsules prepared with polylactic acids or copoly(lactic/glycolic) acids and in vivo degradation of these polymers" *Chem Pharm Bull*, 36: 2576–2581.

Van De Weert, M., et al., 2000. "Protein instability in PLGA microparticles" *Pharm Res*, 17: 1159–1167.

Knutson, B.L., et al., 1996, "Preparation of microparticulates using supercritical fluids" Chpt. 3 in Microparticulate Systems for the Delivery of Proteins and Vaccines. Cohen, S. and Bernstein, H. (Eds.) Marcel Dekker, Inc., New York, USA, pp. 89–125.

Mumenthaler, M., et al., 1994, "Feasibility study on spray–drying protein pharmaceuticals: rhGH and t-PA" *Pharm Res*, 11: 12–20.

Maa, Y.-F., et al., 1998. "Spray–drying of air–liquid interface sensitive recombinant human growth hormone" *J Pharm Sci*, 87: 152–159.

Rodriguez, L., et al., 1999. "Description and preliminary evaluation of a new ultrasonic atomizer for spray–congealing processes" *Int J Pharm*, 183: 133–143.

Bittner, B. et al., 1999. "Ultrasonic Atomization for spray drying: a versatile technigue for the preparation of protein loaded biodegradable microspheres" *J Microencapsulation*, 16: 325–341.

Thies, C., 1996. "A survey of microencapsulation processes" Chapter 1 in Microencapsulation: Methods and Industrial Applications, Benita, S. (Ed.), Marcel Dekker, Inc., New York, USA, pp. 1–19.

Benoit, J.-P., et al., 1996. "Biodegradable microspheres: Advances in production technology" Chapter 3 in Microencapsulation: Methods and Industrial Application. Benita, S. (Ed.), Marcel Dekker, Inc., New York, USA, pp. 35–72.

Zhu, G., et al., 2000. "Stabilization of proteins encapsulated in injectable PLGA" *Nat Biotechnol*, 18: 52–57.

Kim, H.K. et al., 1999. "Microencapsulation of human growth hormone within biodegradable polyester microspheres: protein aggregation stability and incomplete release mechanism" *Biotechnol Bioeng*, 65: 659–667.

Reslow, M., et al., 2002. "Polymer coated starch microspheres as protein delivery system" 29th International Symposium on Controlled release of Bioactive Materials, Seoul, Korea, #698.

Yeo, Y., et al., 2002. "Solvent exchange method: A novel microencapsulation technique" 29th International Symposium on Controlled Release of Bioactive Materials, Seoul, Korea, #294.

Berger, H.L., 1998. Ultrasonic Liquid Atomization, Chapters 1 and 8. Partridge Hill Publishers, Hyde Park. NY.

Wise, D.L., et al. eds., 1995. Encyclopedic handbook of biomaterials and bioengineering, Part A: Materials, vol. 2., Marcel Dekker, Inc. New York, pp. 1037–1038.

Sah, H., 1997. "Microencapsulation techniques using ethyl acetate as a dispersed solvent: effects of its extraction rate on the characteristics of PLGA microspheres" *J Controlled Release*, 47: 233–245.

Sah, H., 1999. "Protein instability toward organic solvent/water emulsification: implications for protein microencapsulation into microspheres" *PDA J Pharm Sci Technol*, 53: 3–10.

Sturesson, C., et al., 2000. "Incorporation of protein in PLG microspheres with retention of bioactivity" *J Controlled Release*, 67: 171–178.

Soppimath, K.S., et al., 2001. "Encapsulation of antihypertensive drugs in cellulose–based matrix microspheres: characterization and release kinetics of microspheres and tableted microspheres" *J Microencapsulation*, 18: 397–409.

Sah, H., et al., 1996. "A novel method of preparing PLGA microcapsules utillizing methylethyl ketone" *Pharm Res*, 13: 360–367.

Yeo, Y., et al., 2001. "Microencapsulation methods for delivery of protein drugs" *Biotechnol Bioprocess Eng*, 6: 213–230.

Price, J., 2000. "Gelatin", in Handbook of Pharmaceutical Excipients, 3rd ed., A.H. Kibbe, ed., Pharmaceutical Press, London, UK, pp. 215–217.

Edsman, K., et al., 1998. "Rheological evaluation of poloxamer as an in situ gel for ophthalmic use," *European J Pharm Sci.*, 6:105–112.

Jeong, B., et al., 2002. "Thermosensitive sol–gel reversible hydrogels" *Advanced Drug Delivery Reviews*, 54: 37–51.

Bodmeier, R. et al., 1988. "Solvent selection in the preparation of PLA microspheres prepared by the solvent evaporation method" *Int J Pharm*, 43: 179–186.

Cohen, S., et al. "Controlled delivery systems for proteins based on PLGA microspheres" *Pharm Res*, 8: 713–720.

Teas, J.P., 1968. "Graphic analysis of resin solubilities" *J. Paint Technol.*, 40: 19–25.

Hansen, C.M., 1967. "The three dimensional solubility parameter—Key to paint component affinities: II and III" *J. Paint Technol*, 39: 505–514.

Grinstaff, M.W. et al., 1991. "Air–filled proteinous microbubbles: synthesis of an echo–contrast agent" *Proc. Natl. Acad. Sci. USA*, 88: 7708–7710.

Unger, E.C., et al., 2001. "Local drug and gene delivery through microbubbles" *Progress in Cardiovascular Diseases*, 44: 45–54.

Atchley, A. et al., 1988. "Acoustic Cavitation and Bubble Dynamics" in Ultrasound: Its chemical, physical, and biological effects, Suslick, K.S. ed., Wiley–VCH, Weinheim, Germany, pp. 1–19.

Mason, T.J., 1990. "Introduction," In Chemistry with Ultrasound. Critical Reports on Applied Chemistry, vol. 28, T.J. Mason, ed., Society of Chemical Industry, Elsevier Applied Science, London, UK, pp. 1–13.

Watkin, K.L. et al., 2002. "Multi–modal contrast agents: A first step" *Academic Radiology*, 9: S285–S289.

FIG. 1/9
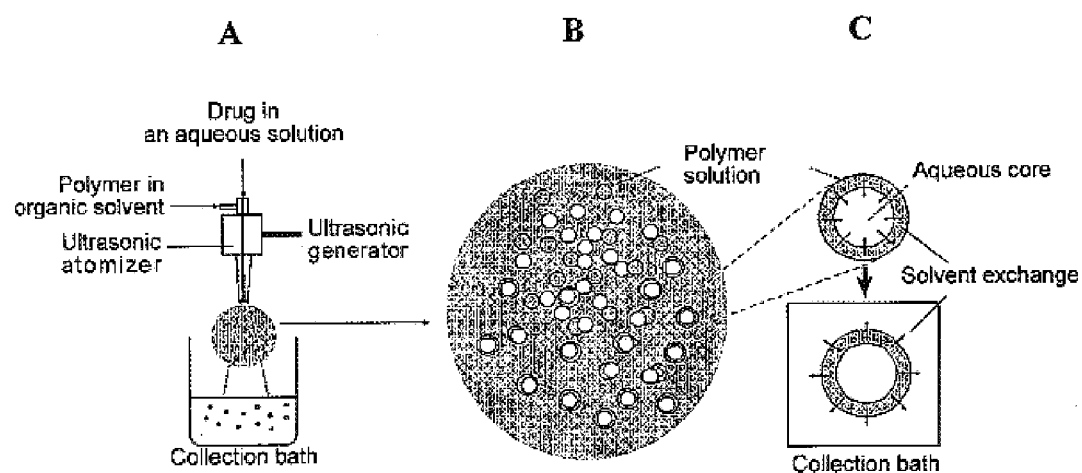

FIG. 2/9
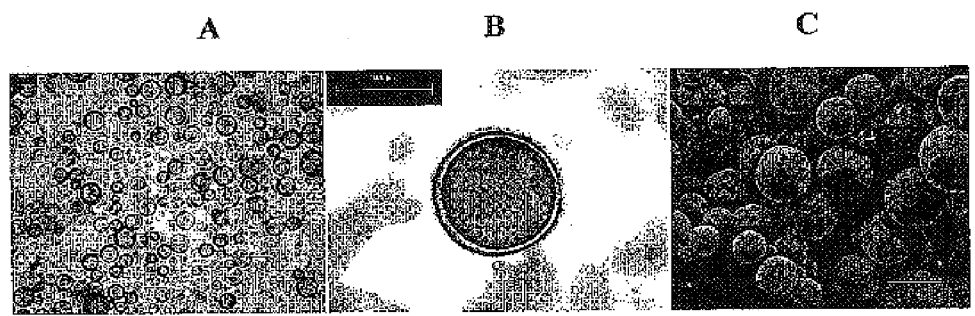

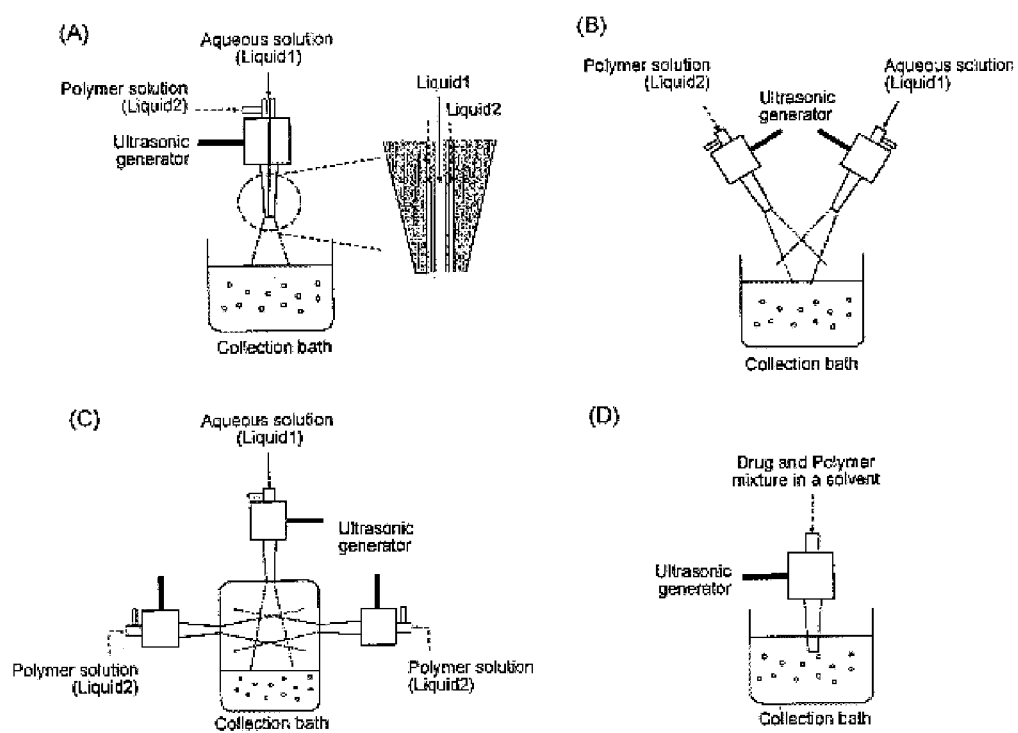
FIG. 3/9

FIG. 4/9
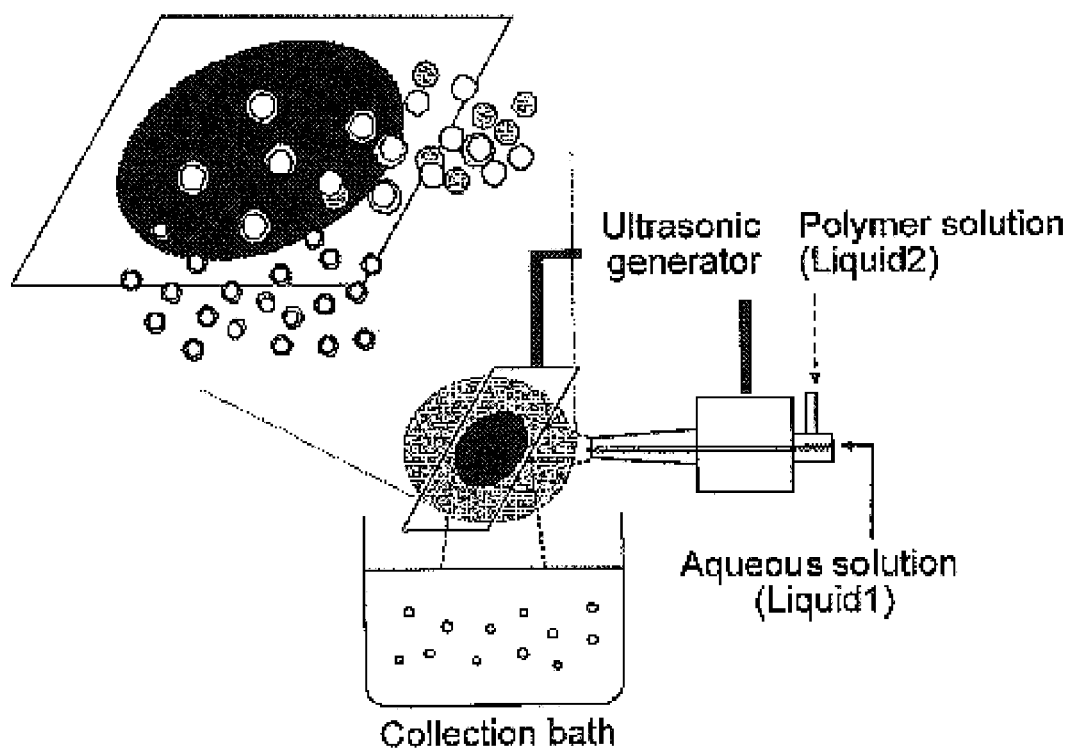

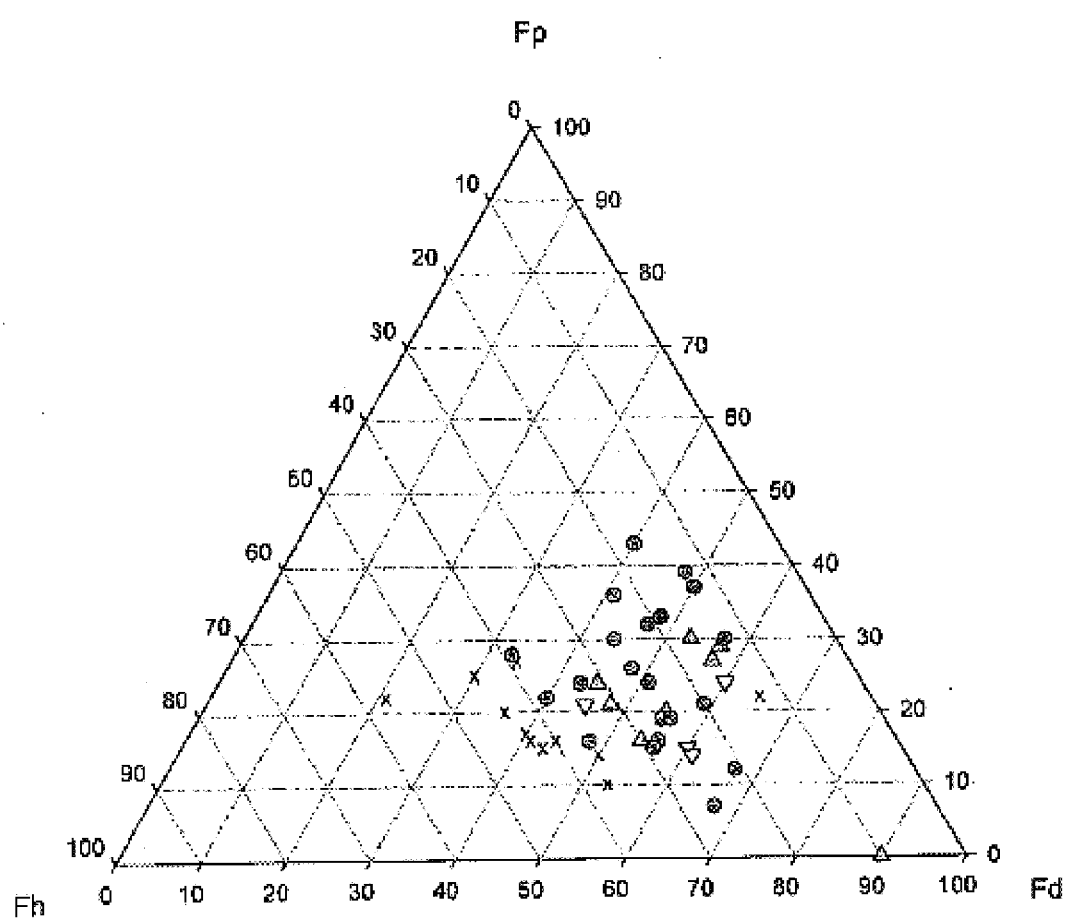
FIG. 5/9

FIG. 6/9
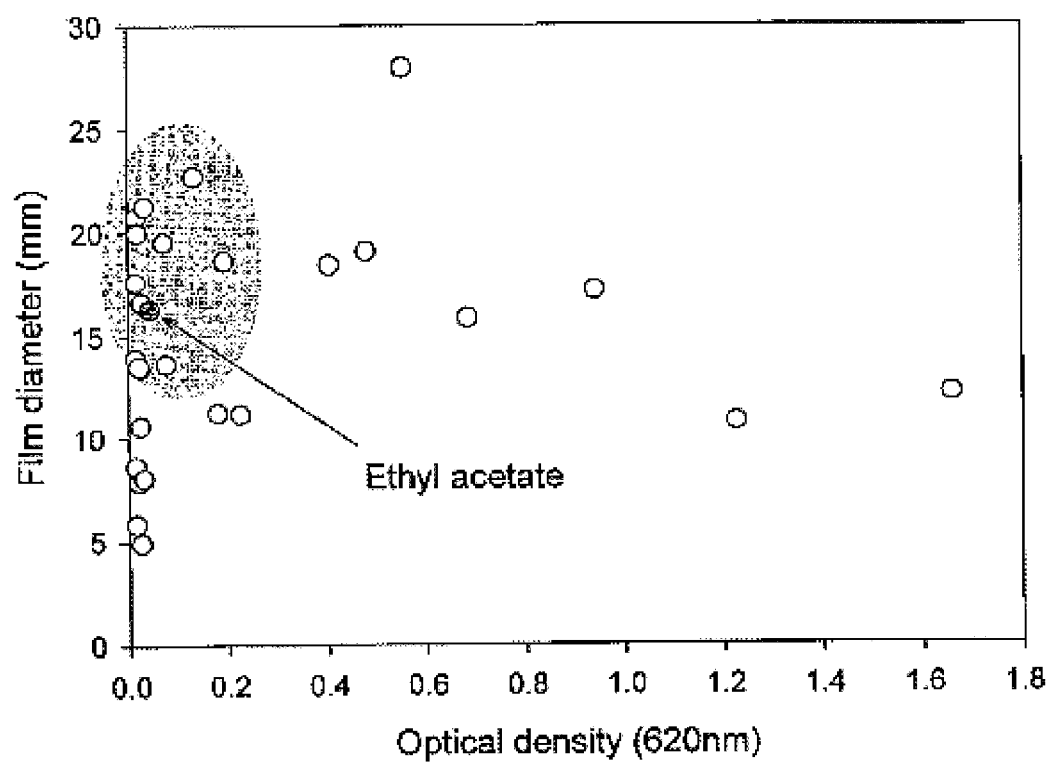

FIG. 7/9
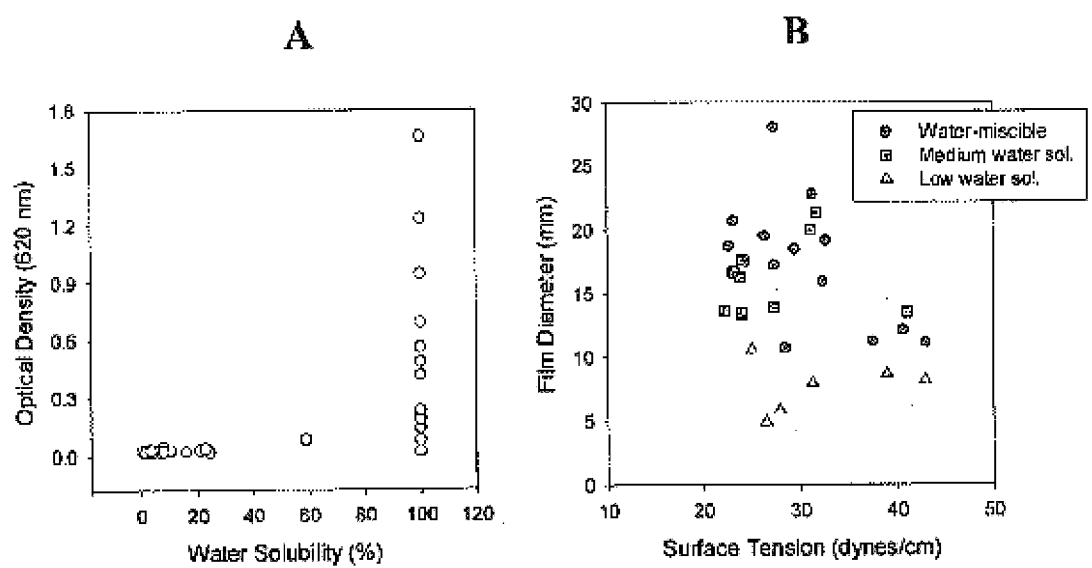

FIG. 8/9
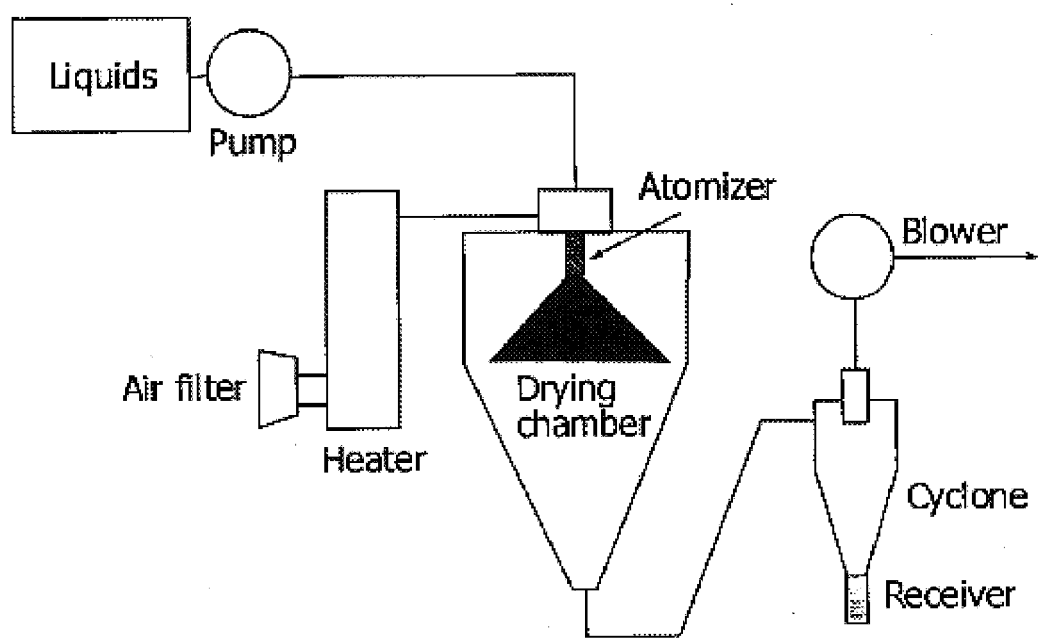

FIG. 9/9
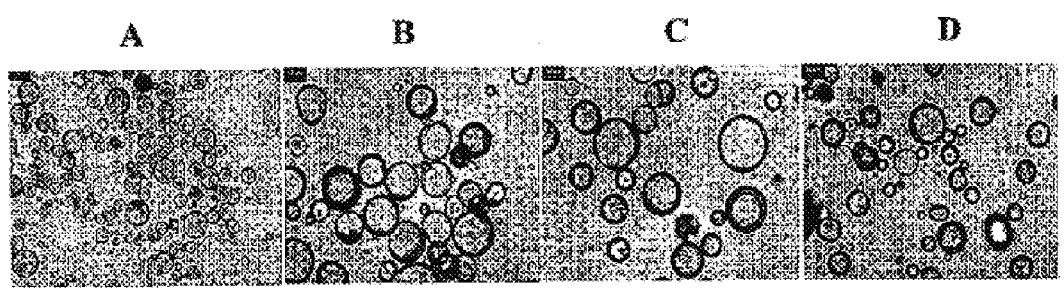

MICROENCAPSULATION USING ULTRASONIC ATOMIZERS

REFERENCE TO RELATED APPLICATIONS

This application claims the benefit under 35 USC 119(e) of U.S. Provisional Application No. 60/365,411, filed Mar. 19, 2002, and is a continuation-in-part of U.S. Ser. No. 10/017,338, filed Dec. 13, 2001, now U.S. Pat. No. 6,599, 627, which claims the benefit under 35 USC 119(e) of U.S. Provisional Application 60/254,920, filed Dec. 13, 2000, and U.S. Provisional Application 60/294,263, filed May 31, 2001.

FIELD OF THE INVENTION

The present invention relates to pharmaceutical compositions and methods of drug delivery. The invention especially relates to methods and compositions for controlled release of easily denatured drugs utilizing microcapsules.

BACKGROUND OF THE INVENTION

Microencapsulation technologies have advanced significantly during the last few decades and the current technologies are at such a level that drugs can be delivered at predetermined rates for days and years depending on applications. These advances, however, usually apply only to low molecular weight drugs. Microencapsulation of high molecular weight drugs, such as peptides and proteins, is still complicated due to the intricate nature of their physical and chemical properties. Of these, protein-based pharmaceuticals have become especially important since mass production of such drugs has been enabled by recombinant DNA technology. Furthermore, completion of the human genome project is expected to bring about an improved understanding of the therapeutic roles of specific proteins, which should lead to numerous new protein drugs.

Since the early promise of sustained delivery of proteinaceous drugs [1], studies on protein microencapsulation have increased exponentially. Some of the early efforts succeeded in bringing the first microparticle product for peptide delivery (LUPRON DEPOT) onto the market [2, 3]. Not long after the commercial success of this product, however, it was recognized that the susceptibility of most proteins to environmental stresses would pose serious barriers to development of microparticle systems for proteins. Despite all the obstacles, protein microencapsulation is still an attractive approach, especially when such pharmaceuticals cannot be delivered via oral routes. Also, the need for infusions or frequent drug injections calls for the development of long-term delivery systems.

Current technologies commonly used in the preparation of microparticles for controlled drug delivery are summarized below, each of which has its own advantages and limitations.

Emulsion—solvent evaporation or extraction

Coacervation (Simple and complex coacervation)

Hot melt microencapsulation (congealing)

Interfacial cross-linking and interfacial polymerization

Spray drying

Supercritical fluid

The emulsion (solvent evaporation or extraction) methods utilize volatile organic solvents for dissolving water-insoluble polymers, such as poly (lactic acid-co-glycolic acid) (PLGA). Microdrops are produced when a mixture of a drug and a polymer solution is emulsified in a continuous phase, which is usually water. The microdrops become microparticles after solvent removal. A double emulsion process is commonly used for encapsulation of water-soluble drugs such as protein or peptide. Both solid/oil/water (s/o/w) and water/oil/water (w/o/w) systems are used depending on the type of protein drug. In the solvent evaporation method, the organic solvent is removed by evaporation at a raised temperature and/or under vacuum. See, for example, U.S. Pat. No. 3,523,906 (issued to Vrancken, et al. [41]). In the solvent extraction method, the organic solvent is extracted into a large volume of continuous phase, thereby turning the emulsion drops into solid polymer microspheres. See, for example, U.S. Pat. No. 4,389,330 (issued to Tice, et al. [5]). The organic solvents conventionally employed in this method are typically chlorinated hydrocarbons, such as methylene chloride. In both methods, the use of chlorinated solvents often becomes a substantial drawback for environmental and human safety reasons. FDA guidelines for the residual solvents limits the permitted daily exposure to 6 mg per day for methylene chloride. In addition, the loading capacity of microspheres prepared by this method is in general very low. Furthermore, the way emulsions are created increases not only the total interfacial area the bioactive substances are subjected to, but also extensive shear and cavitation stress, which may be destructive to bioactive substances [6].

To minimize such loss of activity of the bioactive substances, it is proposed to make microspheres at very low temperatures. See, e.g., U.S. Pat. No. 5,019,400 (issued to Gombotz, et al. [7]). Biodegradable polymer is dissolved in an organic solvent, such as methylene chloride, together with a protein powder and then atomized over a bed of frozen ethanol overlaid with liquid nitrogen. The microdrops freeze upon contacting the liquid nitrogen and then sink onto the frozen ethanol layer. As the ethanol layer thaws, the frozen microspheres sink into the ethanol. The methylene chloride solvent in the microspheres then thaws and is slowly extracted into ethanol, resulting in hardened microspheres containing proteins and polymer matrix. Clearly, this method can be costly and laborious, especially for scaled-up production.

The coacervation method is based on salting out (or phase separation) of polymers from a homogeneous solution into small drops of a polymer-rich phase upon addition of extra substances. For example, when an aqueous polymer solution (e.g., gelatin or carboxymethylcellulose) is partially dehydrated (or desolvated) by adding a strongly hydrophilic substance (e.g., sodium sulfate) or a water-miscible non-solvent (e.g., ethanol, acetone, dioxane, isopropanol, or propanol), the water-soluble polymer is concentrated to form the polymer-rich phase. This is known as simple coacervation. If water-insoluble drug particles are present as a suspension or as an emulsion, the polymer-rich phase is formed on the drug particle surface to afford a capsule. In complex coacervation, the polymer-rich complex (coacervate) phase is induced by interaction between two dispersed hydrophilic polymers (colloids) of opposite electric charges. Since electrostatic interactions are involved, it is important to control the pH of the medium in order to control the charges of the polymers.

In hot melt microencapsulation (also called congealing), a drug is mixed with a polymer, which is melted at high temperatures. The mixture is then suspended in a non-miscible solvent with continuous stirring at a temperature several degrees above the melting point of the polymer. After the emulsion is stabilized, the system is cooled until the polymer particles are solidified. This method requires the drug to be stable at the polymer melting temperature.

Interfacial cross-linking and interfacial polymerization employ two reactive phases that can form a solid boundary at their interface, which becomes the surface of microparticles. For interfacial cross-linking, the polymer must possess functional groups that can be cross-linked by ions or multi-functional molecules contained in a continuous phase. Interfacial polymerization requires two reactive monomers dissolved in immiscible solvents that can be polymerized at the interfaces. Capsules are collected after quenching the polymerization reaction with a third phase.

Spray-drying involves spraying a mixture of a drug and a polymer and evaporating the solvent in a drying chamber to solidify the atomized drops. This seemingly simple process has not been widely used in the pharmaceutical industry due at least in part to difficulties in the scale-up process. The parameters optimized in the laboratory scale spray dryer do not usually work for the industrial scale spray dryer. Moreover, the temperature of inlet gas that is used for drying the microdrops can reach 90–150° C. [9, 10], which may not be tolerable for encapsulation of heat-sensitive biomaterials.

Ultrasonic atomizers have reportedly been used for microparticle formation in connection with the spray-drying or spray-congealing techniques discussed hereinabove. In one example, the ultrasound energy was used to break up drug and carrier mixture into microparticles [11]. A lipid excipient and a drug were mixed at a temperature higher than the melting point of the excipient. The resulting fluid was poured onto the oscillating surface, and the liquid was atomized into small drops upon hitting the surface. The microdrops were collected in a cold chamber in which the liquid drops were solidified (spray-congealing). In another example, a water/oil (w/o) emulsion consisting of an aqueous bovine serum albumin (BSA) solution and PLGA solution in methylene chloride was atomized using an ultrasonic atomizer adapted to a conventional spray dryer [12]. Thus formed microspheres were collected directly after the solvent evaporation (spray-drying). For example, protein loaded microspheres were produced using an ultrasonic atomizer (U.S. Pat. No. 5,389,379, issued to Dirix et al. [13]). They collected the particles in a non-solvent bath to remove the organic solvent. The hardened drops were subsequently transferred into the second non-solvent to harden the microspheres.

Supercritical fluids have recently been utilized for their unique characteristics: high compressibility and liquid-like density. Microparticles have been prepared by either rapid expansion of supercritical solutions (RESS) or supercritical antisolvent crystallization (SAS) [8]. RESS exploits the liquid-like solvent power of the supercritical fluids whereas SAS uses supercritical fluid as an antisolvent. Carbon dioxide is most commonly used because it is environmentally benign, relatively non-toxic, non-inflammable, and inexpensive, and the condition for the critical fluid is easily attainable. RESS is limited by the requirement that all solutes should be soluble in the supercritical fluid. For this reason, RESS may not be used to make protein loaded polymeric microcapsules. By contrast, the SAS method utilizes the supercritical fluid as an anti-solvent that causes precipitation of the solids. Therefore, the SAS method is suitable for solids that are difficult to solubilize in supercritical fluids, such as peptides and proteins. However, the supercritical fluid approach is in its infancy and it is as yet hard to anticipate mass-production of microparticles using this method.

In discussing different approaches of microencapsulation, it is useful to understand the terms commonly used in the microencapsulation field. Microparticles can be categorized as "microspheres" and "microcapsules". The term "microspheres" usually refers to monolithic type formulations in which the drug molecules are dispersed throughout the polymeric matrix [14]. On the other hand, the term "microcapsules" refers to reservoir devices in which a drug-containing core is surrounded by a continuous polymeric layer, shell, or membrane. Depending on the geometry of the core, microcapsules can be multinuclear microcapsules, where multiple drug cores are embedded throughout the polymer matrix, or mononuclear microcapsules, for which a single drug core is surrounded by the polymer membrane [15].

One of the disadvantages of microspheres or multinuclear microcapsules is that degradation products of the polymer can easily build up to generate acidic microenvironments within the microparticles, which can be undesirable for acid-labile drugs [16]. Furthermore, the presence of abundant polymer in proximity to a large amount of drug can cause unfavorable interaction between two substances. It can be a significant problem when it comes to protein drugs, which are highly susceptible to denaturation due to hydrophobic interactions with the polymer [17].

In this regard, mononuclear microcapsules can provide a number of advantages. First of all, microcapsules provide much more drug reservoir space than microspheres. The reservoir space can accommodate protective excipients as well as drugs. Also, drugs located in the single core are not in extensive contact with the polymer, but only those on the surface are exposed to the degrading polymer. The degradation products of the polymer would not build up within the microcapsules because they are more likely to diffuse out to the release medium rather than to the core structured by the constituent excipients. In addition, the release profile can be further modified by building heterogeneous layers of membranes.

Most previous methods described to date afford either microspheres or multinuclear microcapsules. Most methods produce a mixture of a drug and a polymer in forms of homogeneous solution, suspension, or emulsion, prior to breaking it up into microdrops. It is the mechanics leading to the fragmentation of the mixture that characterizes each method. That is, emulsification in an emulsion method, air atomization in spray drying, and a change in solubility of the polymer induced by the extra substance in the coacervation method.

Mononuclear microcapsules can be produced by the interfacial cross-linking and interfacial polymerization methods. However, the complexity of the procedures and handling of the unreacted monomers can be issues that make them impractical. Gustavsson et al. [18] describe a method to coat starch microparticles with a polymer shell for control of the drug release profile. The polymer coating is obtained by suspending the core microparticles in an air-suspension coater providing a polymer solution [19]. However, the time and the labor required to finish the multi-step procedures may become obstacles when modifying the production scale.

Accordingly, it is an object of the present invention to identify a novel microencapsulation technique that affords such desirable features as the following: (a) entrapment of bioactive substances in microparticles in such a way that their bioactivity is maintained; (b) avoidance of exposure of the encapsulated bioactive substances to undesirable conditions, including a high water-oil interfacial area, contact with the toxic organic solvents or reactive radicals, mechanical stresses, and both extremes of temperature; (c) avoidance of extensive contacts between the bioactive substance and the hydrophobic polymer matrix and/or accumulation of the degradation products of the polymer, which are likely to compromise the stability of the encapsulated drugs; and (d) microencapsulation accomplished in a single-step, thereby permitting easy scale-up of production.

SUMMARY OF THE INVENTION

The present invention achieves the objectives identified above by employing atomization technology, particularly ultrasonic atomization, in conjunction with 'solvent exchange' to produce microencapsulated particles. A microencapsulation method based on solvent exchange, which employs ink-jet technology, has been described previously, see, e.g., U.S. Patent Publication 2002/0160109 A1. Surprisingly, it has now been observed that the solvent exchange process can also be achieved by simultaneously producing a large number of drops of aqueous and polymer solutions, and spatially concentrating them to facilitate collision among the drops.

Accordingly, in one aspect of the invention a method for preparing a microencapsulated composition is contemplated. Such a method comprises: (1) providing an aqueous solution containing a composition to be encapsulated dissolved therein; (2) providing a polymer solution containing a water-insoluble polymer dissolved in a hydrophilic solvent; (3) generating a plurality of first microdroplets from the aqueous solution; (4) generating a plurality of second microdroplets from the polymer solution, wherein the first and second microdroplets are generated by at least one atomizing device; and (5) contacting the first and second microdroplets to form a plurality of pre-encapsulant particles. The pre-encapsulant particles have a core domain containing the aforementioned composition and an outer layer containing the polymer, such that solvent exchange occurs between the core domain and the outer layer thereby forming a polymer shell around the encapsulated composition.

Atomizers for use in conducting a production method of the present invention include those that employ centrifugal, pressure, kinetic, and sonic energy. Preferred atomizers are ultrasonic ones, as illustrated by examples hereinafter. Substances that can be encapsulated include any water-soluble compound, but particularly interesting are bioactive substances, such as low molecular weight drugs, proteins, oligonucleotides, gene, and polysaccharides. A particularly advantageous property of microcapsules produced according to the present invention is that they can exhibit controlled release properties.

A number of atomizer configurations for use in generating microcapsules according to the present invention are contemplated. A particularly surprising and useful configuration is one in which a coaxial ultrasonic atomizer is submerged into an aqueous collection bath. In this configuration, immediate solvent exchange can occur between the microparticles and the bath in addition to the solvent exchange that can occur between core and shell domains.

Pre-encapsulant particles formed by a method of the present invention can be hardened, i.e., the polymer-containing shell can be solidified, through solvent exchange. Such hardening can be due to solvent exchange between the aqueous core and polymer-containing shell of the particles and/or between the shell and surrounding bath. Alternatively, solvent removal from the polymer-containing shell can be effected by spray drying or freeze drying techniques.

In another aspect of the present invention, microbubbles can be produced using an atomizer. In this aspect, hydrophobic drugs can be loaded alongside polymer in a single phase. Microcapsules containing hydrophobic compounds within a non-aqueous core can also be made.

BRIEF DESCRIPTION OF THE DRAWINGS

FIG. 1 schematically illustrates a solvent exchange method of the present invention as implemented with a coaxial ultrasonic atomizer. A plurality of microdrops of each solution is produced by the atomizer (A). Collision occurs among the drops resulting in coalescence (B). Solvent exchange begins as soon as two different microdrops come in contact (C).

FIG. 2 shows several views of microcapsules typically produced by a method of the invention. Panels A and B show bright field microscopic pictures and Panel C shows scanning electron microscopic pictures of mononuclear microcapsules produced by an ultrasonic atomizer according to principles of the present invention. Scale bars: 100 $\mu$m.

FIG. 3 depicts four different configurations of ultrasonic atomizer assemblies contemplated for generation of microcapsules according to principles of the present invention.

FIG. 4 schematically illustrates particle size reduction using an extra piezo device interposed between the ultrasonic atomizer and a collection bath.

FIG. 5 depicts a plot of various solvents as a function of the fractions of their dispersion force ($f_d$), polarity ($f_p$), and hydrogen bonding ($f_h$) for use in hydrophilic solvent selection. (●) Good solvent; (▲, Δ) Intermediate solvent; and (X) Poor solvent.

FIG. 6 illustrates selection of hydrophilic organic solvents by the hydrogel method with preferred solvents marked by a shadow.

FIG. 7 illustrates selection of hydrophilic solvents using optical density as a measure of membrane quality (Panel A) and film diameter reflecting the degree of spreading (Panel B).

FIG. 8 depicts a schematic representation of the use of a spray dryer apparatus according to principles of the present invention.

FIG. 9 illustrates bright field microscopic images of microcapsules produced with an ultrasonic atomizer using 2% PLGA solution in ethyl acetate and several combinations of aqueous solution and collection bath as set forth in Example 1.

DETAILED DESCRIPTION OF THE INVENTION

The solvent exchange method for forming microcapsules is based on a phenomenon that a solid polymer film forms at the interface between an aqueous solution and a solution containing a water-insoluble polymer upon contact of the two solutions as a result of phase separation of the polymer. This method permits production of mononuclear drug-containing microcapsules (consisting of a single aqueous core surrounded by a thin biodegradable polymer membrane) whenever solvent exchange occurs between a polymer-containing solvent shell surrounding an aqueous core microdrop containing the drug. A solvent exchange method of microcapsule formation has been previously described by Y. Yeo et al. in U.S. Ser. No. 10/017,338, the pertinent disclosure of which is incorporated herein by reference.

Formation of a polymer film enveloping the surface of an aqueous drop depends on spreading of the polymer solution on the aqueous surface and subsequent phase-separation of the water-insoluble polymer. It is observed that spreading of the polymer solution is mainly dictated by physical properties of the hydrophilic or water-miscible polymer solvent. On the hydrogel surface, the polymer solution is exposed to two kinds of interfaces: an interface with a hydrogel (which consists of >90% of water, so it is basically an interface with water) and an interface with air. For favorable spreading of the polymer solution over the aqueous surface, the solvent is required to have a low interfacial tension against both water and air (i.e., surface tension). Phase-separation of the polymer film is a result of mass transfer between the polymer (e.g., organic) solvent and water (i.e., solvent exchange) leading to a decrease in the solubility of the polymer in the solvent. Organic solvents should be miscible with water to a certain degree in order to cause instant phase-separation of the polymer film. Once a suitable solvent is determined, reservoir type microcapsules can be formed by applying the drops of polymer solution onto the drug-containing aqueous drops.

One way to achieve this objective is to produce a plurality of drops of the aqueous and the polymer solutions and induce collision among the drops. The collision is followed by coalescence of the drops. The hydrodynamic fates of the two liquid drops are determined by the relative surface tensions of the liquids. The organic solvent preferentially deforms and spreads on and around the aqueous drop upon contact, while the aqueous drop having a higher surface tension relative to that of the organic solvent tends to maintain its spherical shape.

This process has been previously described in connection with use of ink-jet nozzles. See, Y. Yeo, et al., U.S. Ser. No. 10/017,338. In this approach, two ink-jet nozzles: one generating aqueous drops and the other producing drops of the polymer solution, are aligned to allow collision between pairs of microdrops emerging from each nozzle. Immediately following collision, the polymer drop spreads on the aqueous drop and solvent exchange between two liquids forms a polymer membrane on the surface of the aqueous drop.

In the present invention, a coaxial ultrasonic atomizer can be employed to produce a plurality of drops of each solution (FIG. 1, Panel A). Two liquids comprising aqueous drug solution and the biodegradable polymer dissolved in (an) organic solvent(s) flow through the ultrasonic atomizer. As the atomizer vibrates at an ultrasonic frequency, both liquids form a double layered film on the surface of the atomizer tip and are simultaneously fragmented into a large number of drops. Collision occurs among drops in proximity, which is followed by coalescence of the drops (FIG. 1, Panel B). For this purpose, a coaxial atomizer is preferably used because it efficiently generates a space where the drops are highly populated, and thus collision of heterogeneous drops is very likely. The solvent exchange process begins as soon as the two microdrops come in contact (FIG. 1, Panel C).

Hardening of the microcapsules can be completed in a water bath as the solvent exchange process is accelerated in the presence of an abundance of water. The air and the water bath can thus be called primary and secondary continuous phases, respectively. One of the unique aspects of this approach is that solvent exchange occurs very fast and microcapsule formation is complete in a matter of seconds. Exemplary microcapsules are shown in FIG. 2 under different levels of magnification. The microcapsules appear transparent when observed by a bright field microscope, since the surrounding polymer layer is only a membrane, as shown in Panels A and B. The main spherical bodies of the microcapsules appear blue when stained with Coomassie Blue, indicating that the aqueous cores consist of the aqueous encapsulation solution. The scanning electron microscopic image (Panel C) shows that the surface of the microcapsules appears smooth and free of major defects, indicating that solvent exchange occurring at the interface of the aqueous core and the polymer-containing organic solvent shell produces a continuous polymer membrane. Typical particles sizes for microcapsules produced according to the present invention are in the range of about 0.1 to about 500 $\mu$m.

1. Principles of Ultrasonic Atomization

When a liquid film is introduced onto a vibrating surface, such that the direction of vibration is perpendicular to the surface, the liquid film absorbs the vibration energy and creates unique capillary waves, which form regularly alternating crests and troughs in the liquid film [22]. Beyond the critical amplitude, the capillary waves cannot maintain their stability, and the waves collapse and tiny drops of liquid emerge from the top of the waves.

An ultrasonic atomizer is a device used to generate such vibrations leading to atomization of a liquid [23]. The atomizer body consists of three principal sections: front horn, the atomizing section; rear horn, the rear section, and a section consisting of a pair of disc-shaped piezoelectric transducers. Working in unison, these three elements provide means for creating the vibration required to atomize liquids delivered to the atomizing surface. Liquid enters through a fitting on the rear, passes through the tube and then the central axis of the front horn. Finally, the liquid reaches the atomizing surface where atomization takes place. Piezoelectric transducers convert electrical energy provided by an external power source into high-frequency mechanical motion [22]. The vibration energy applied to the atomizing surface lets the liquid overcome the surface tension and spread on the surface forming a liquid film. The liquid film absorbs the underlying vibration energy and generates capillary waves. When the amplitude of the capillary waves exceeds a critical value, the waves collapse ejecting small drops of the liquid.

Ultrasonic spray technology has been employed in industrial and research applications related to the electronics and biomedical areas, mainly for surface coating and liquid dispensing. [22]. In the biomedical industry, the ultrasonic atomizers have been used for coating the interior of blood-collecting tubes with anti-coagulants, applying adhesives to sutures, or dispensing reagents into well-plates for diagnostic testing [22].

The popularity of the ultrasonic atomizer in such areas is mainly attributed to its ability to produce drops of small size and low inertia. The velocity of the drops produced from an ultrasonic atomizer is 1~10% that of a hydraulic or air-atomizing nozzle, and this virtually eliminates overspray problems. Another advantage of ultrasonic atomization is that the mechanical stress caused by the vibration is relatively minor so that it does not render bioactive substances inactive [22]. Ultrasonic atomizers operate at low energy levels, which are unlikely to compromise the viability of biological materials, such as blood, antibodies, and bacteria.

2. Atomizer Configurations

The configuration of the atomizers can be varied without limit as long as it guarantees collision among liquid microdrops. A coaxial atomizer is preferably used because it efficiently generates a space where the drops are highly populated, and thus collision of heterogeneous drops is most likely (FIG. 3-A). In a coaxial atomizer, two liquids flow under the influence of a single ultrasonic generator. One liquid flows through the inner nozzle, and the other flows through the outer one. Both liquids delivered to the same atomizing surface are broken into microdrops as the vibration energy is applied on the surface. Coalescence occurs among the liquid drops in close proximity. Microencapsulation is not affected by the pathway each liquid is allowed to follow. When an extended contact between the two liquids does not cause a stability problem for the drug, the procedure can be performed without a coaxial cable. In this system, the liquid inlets are not limited to two, but can be expanded as many as desired.

Two separate atomizers can be arranged in such a way that two sprays of microdrops can collide in air (FIG. 3-B). In this configuration, the distance from each atomizer to the space where the collision takes place is important, since it determines the population density of drops of two liquids in the space and thereby the yield of microencapsulation. Each spray of microdrops can be produced in a thin sheet form and arranged to cross each other so that the probability of collision can be maximized. In a separate atomizer system, the number of atomizers is not limited to two, but can be expanded to as many as desired. See FIG. 3-C.

A closed receptacle can be used to prevent airflow around atomizers, which can cause difficulty in controlling the trajectory of the liquid spray (FIG. 3-C). Furthermore, vacuum or heat can be applied into the closed receptacle to facilitate solvent removal.

It was a totally unexpected finding that microcapsules can also be produced by submerging the atomizer in a collection bath to induce the solvent exchange directly by contact between polymer drops and the collection bath (FIG. 3-D). Thus formed microparticles are mononuclear microcapsules containing bath materials in the core. Lipophilic/hydrophobic drugs can be loaded into the microcapsules by co-dissolving the drugs with the polymer. Hydrophilic drugs can be loaded into the microcapsules by generating them in an aqueous bath containing the drug(s) to be encapsulated.

Another unexpected finding was that particle size of the microcapsules can be reduced by fragmenting the embryonic pre-encapsulant particles before microcapsule formation is complete. As shown in FIG. 4, embryonic particles emerging from the atomizer are broken into smaller particles upon hitting an extra piezoelectric device. The piezoelectric surface can assume any form including sheet, cylinder, sphere, and combinations thereof. An exemplary piezoelectric device is commercially available from Sono Tek Corp. (Milton, N.Y.).

3. Encapsulating Polymer

For a long-term delivery of bioactive substances, biodegradable polymers are preferable, especially when their degradation products are known to be innocuous or biocompatible. They need not be surgically removed at the end of a treatment. Commonly used biodegradable polymers, which have been investigated for the controlled delivery of protein drugs, include homopolymers of poly(lactic acid) (PLA) or poly(glycolic acid) (PGA), poly(lactic acid)-co-(glycolic acid) (PLGA), poly(ortho esters), and polyanhydrides. Due to the biocompatibility and the long history of clinical applications, PLGA and PLA are most preferably used. Other biodegradable polymers that can be used include polycaprolactone, polycarbonates, polyesteramides, poly (amino acids), poly(dioxanones), poly(alkylene alkylate)s, polyacetals, polycyanoacrylates, biodegradable polyurethanes, blends and copolymers thereof. In addition, non-biodegradable polymers can be used. Examples include polyacrylates, polymethacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, blends and copolymers thereof.

4. Polymer Solvents

Since a key attribute of the present invention is solvent exchange at the water-solvent interface in relation to spreading of the solvent over the aqueous surface, the selection of an appropriate polymer solvent is of utmost importance. The hydrophilic, e.g., organic and water-miscible, solvent for the solvent exchange method should meet the following requirements.

- The solvent should possess the right solvency for the polymer (e.g., PLGA).
- The solvent should be able to spread out favorably on the aqueous surface.
- The solvent should be miscible with water to a certain degree, thus allowing fast phase separation of the polymer.

Solvent screening can begin with the Hildebrand solubility parameters of the organic solvents. The solubility parameter of PLGA (lactic acid:glycolic acid=58:42) is known to be 16.8~18.7 $MPa^{1/2}$ [24]. When 60 solvents having the Hildebrand solubility parameter of 16~24 MPa are screened, however, only half of them are able to produce clear PLGA solutions, and the rest are poor solvents or marginally able to swell the PLGA. The results are summarized on a triangular graph according to the Teas method (FIG. 5). In Teas method, fractional parameters are calculated as:

$$f_i=100\delta_i/(\delta_d+\delta_p+\delta_h)$$

where i=d, p, or h.

where $\delta_d$, $\delta_p$, and $\delta_h$ are Hansen's multicomponent solubility parameters which stand for the contributions from dispersion forces, polar interactions, and hydrogen bonding, respectively. In the triangular graph, good solvents for PLGA are localized in a region of relatively low $f_p$ and $f_h$ but of high $f_d$. This triangular graph can be used in the future as a quick selection tool of solvents meeting the first requirement. Preferred hydrophilic solvents typically have a Hildebrand solubility parameter in the range of 16 to 26 $MPa^{1/2}$.

Selected good solvents for PLGA can be refined further by a screening method using a hydrogel (the hydrogel method). Solutions of polymer in different solvents are placed on a layer of hydrogel, and thus formed polymer films are evaluated with respect to the diameter and the optical density (FIG. 6). The diameter of the film reflects the degree of spreading of each solvent, and the turbidity allows for evaluation of the quality of the polymer membrane. Solvents that form membranes of relatively large diameters are preferable, since it means that the polymer solution spreads easily. Polymer membranes displaying relatively low optical densities are preferred since high turbidity reflects the formation of a rough and discontinuous precipitate, which is likely to fail in control of the drug release across the membrane.

The quality of the polymer membrane represented by the optical density is linked to the solubility of the solvent in water (FIG. 7-A). Solvents that have low to medium solubility in water (0~60% w/w) result in a transparent and dense membrane, whereas water-miscible solvents (~100% w/w) make a turbid and discontinuous membrane. Preferred hydrophilic solvents have a water solubility of about 5 to about 100%. The spreading capability of the polymer solution represented by the film diameter is related to the surface tension of the solvent (FIG. 7-B). Solvents having relatively low surface tension tend to spread favorably. Surface tension of 30 dynes/cm appeared to be a rough threshold. Therefore, it is also possible to make a quick judgment in solvent selection by examining the surface tension and the water-solubility of the solvent. A preferred hydrophilic solvent has a surface tension of less than about 45 mN/m.

When the solvents were screened with the selection rules described above, ethyl acetate was chosen as one of the best solvents for the solvent exchange method. The basic parameters examined in the screening are listed in Table 1.

TABLE 1

Parameters used for solvent screening. Ethyl acetate is used as an example.

Ethyl acetate ($CH_3COOC_2H_5$)

| | |
|---|---|
| 1. Hildebrand solubility parameter [25] | 18.6 $MPa^{1/2}$ |
| 2. Hansen multicomponent parameters [26] | $f_d/f_p/f_h$ = 56/19/25 |
| 3. Solubility in water [25] | 8% w/w |
| 4. Surface tension [25] | 23.8 dynes/cm |
| 5. Optical density of the PLGA film (at 620 nm) | 0.0438 |
| 6. Film diameter | 16.3 mm |

Relatively hydrophilic organic solvents, such as ethyl acetate, have been used with increasing regularity as an alternative to methylene chloride [19, 27–29]. However, its relatively high solubility in water often makes it difficult to produce dense and regular microspheres using conventional emulsion methods [27] and sometimes requires doping the continuous phase with additional ethyl acetate in order to delay diffusion of the solvent out of the discontinuous phase [30]. For this reason, the morphology of microspheres is far more dependent on the phase ratio (the volume ratio of the organic to aqueous phase) than methylene chloride when ethyl acetate is used in the emulsion method [27]. The hydrophilicity of methylethyl ketone caused the same problem [31].

On the other hand, the solvent exchange method takes advantage of the hydrophilicity of the organic solvent. In fact, utilizing hydrophilic organic solvents is the major feature of the solvent exchange method as previously described. In the solvent exchange method, what makes the microcapsule a sphere is the surface tension of the aqueous solution. Therefore, facile formation of a w/o emulsion is not a requirement for capsule formation. Elimination of such a requirement affords more flexible selection of the organic solvents, which is in turn beneficial to toxicological and environmental safety.

5. Aqueous Phase Components

The aqueous core initiates the phase separation of the polymer, and serves as a reservoir for drug molecules and protective excipients (if necessary). Moreover, it plays an important role in maintaining the mechanical strength of the microcapsules. In this regard, it is preferred to use a hydrophilic polymer that is capable of undergoing the sol-to-gel transition, as the aqueous solution. This unique property, present in many polysaccharides and hydrophilic polymers, makes it possible to process the drug formulation in a liquid state until particle formation and to solidify the particles later by providing appropriate conditions.

For example, sodium alginate, which forms an ionotropic hydrogel in the presence of divalent cations such as calcium, can be used as a base for the aqueous solution. The alginate solution containing a drug substance is ejected from the atomizer and is fragmented into microdrops. Microcapsules formed in air are collected in the aqueous bath containing calcium ions. It appears that calcium ions are able to diffuse into the aqueous core before the polymer membrane is completely sealed by precipitation of the polymer. In addition to alginate, a variety of aqueous polymer solutions can serve the same function. See Table 2.

TABLE 2

Examples of hydrophilic polymers capable of sol-to-gel transformation [32]

| Hydrophilic polymers | Conditions for forming gels |
|---|---|
| Alginate (polyanion) | Calcium (cation) |
| Chitosan (polycation) | Tripolyphosphate (anion) |
| Carboxymethyl cellulose (polyanion) | Aluminium (cation) |
| κ-carrageenan (polyanion) | Potassium (cation) |
| κ-carrageenan (polyanion) | Amines (cation) |
| Pectin (polyanion) | Calcium (cation) |
| Gelan gum (polyanion) | Calcium (cation) |
| Polyphosphazene (polyanion) | Calcium (cation) |
| Gelatin | <35~40° C. (temperature) [33] |
| Poloxamer 407 (20~25%) | >20~30° C. (temperature) [34] |
| Poly(N-isopropylacrylamide) | >32° C. [35] |

The materials that can be used for the aqueous core are not limited to the polymers capable of sol-to-gel transition. A variety of hydrophilic polymers can be included along with drugs in the aqueous solution. The presence of the hydrophilic polymer can increase the viscosity of the aqueous solution, and thus contribute to preventing diffusion of the drug substances into the bath during collection. Especially when the hydrophilic polymer is a polyelectrolyte or has functional groups that can interact with the drug substances, it can play an assistant role in control of the drug release. Examples of suitable hydrophilic polymers are polyethylene glycol (PEG), polyvinylpyrrolidone (PVP), polyvinyl alcohol (PVA), polyoxazoline, polyacrylic acid, polyacrylamide, polymethacrylic acid, deoxyribonucleic acid (DNA), and ribonucleic acid (RNA).

Protective excipients can be included in the aqueous solution to increase the stability of the encapsulated drugs. Examples of such protective excipients include carbohydrates, e.g., sucrose, lactose, mannitol, trehalose, cyclodextrins, surface active agents such as Tweens, stearate salts, Poloxamers, polyvinyl alcohol, hydrophilic polymers such as carboxymethyl cellulose, gelatin, albumin, dextran, polyethylene glycol, or buffer salts such as calcium carbonate, calcium orthophosphate, sodium acetate, magnesium hydroxide, calcium hydroxide, and zinc carbonate.

6. Collection Methods

Microcapsules can be collected in an aqueous bath. Conditions that can induce a sol-to-gel transition of the aqueous core can be provided via the collection bath. When polyelectrolytes such as alginate are included in the aqueous solution, microcapsules are collected in an aqueous bath containing counter-ions such as calciums that can complex with the polyelectrolytes. When the transition is temperature-sensitive, the temperature of the bath can be adjusted appropriately to solidify the aqueous core. Emulsifying agents can be included in the bath to prevent aggregation of the embryonic microcapsules. Polyvinylalcohols, Poloxamers, and Tweens are representative emulsifying agents.

The materials that can be used for the collection bath are not limited to water. Any kind of liquid miscible with the solvent for the polymer but which does not dissolve the polymer can be used for this purpose. Examples are alcohols, ketones, and oils.

When microcapsules are collected in the water bath, it is important to disturb the surface of the water bath efficiently, otherwise, it is possible to accumulate films of polymer solution on the surface, which form a solid layer that obstructs entrance of the microcapsules into the bath. Generally, simple magnetic stirring can easily break the stability of the water surface and allow introduction of the microcapsules into the bath. Vibrating the bath can serve the same purpose and the vibration energy can be provided using an ultrasonic bath or sonication probes submerged in the bath.

Alternatively, the polymer solvent can be removed by evaporation. Extending the path that microcapsules fly in air and/or applying mild heat to the flying microcapsules can dry the solvent before the microcapsules reach the collection bath. The microcapsules can be directly collected as dried particles or can be collected in the bath. The advantages of combining the solvent exchange method with spray-drying are that further hardening procedures are not required and microencapsulation can be performed in a single step. Moreover, the entire procedure is continuous and is, therefore, convenient for aseptic processing and scale-up.

As shown in FIG. 8, ultrasonic atomizers can be employed with a conventional spray-dryer or drying chamber to evaporate the solvent. The polymer solution and the aqueous solution loaded with drugs are atomized using ultrasonic atomizers into a drying chamber of the spray-dryer. Collision among the drops results in microcapsules in air. A stream of warm gas introduced from a separate inlet evaporates the liquids and solidifies the microcapsules. A drying gas (air, nitrogen, or reducing gas), with an inlet temperature of 60° C., is introduced to transport the generated microdroplets at a flow rate of 10 mL/min. The resulting outlet temperature will be lower, e.g., 30° C. After drying, the unheated drying gas flow can be maintained for a predefined period of time (e.g., 30 min, 2 hours, etc.) The formed microcapsules are separated from the carrier gas in a cyclone attached to the drying chamber and collected in a receiver connected to the cyclone. Suitable commercial spray dryers are available from Buchi Analytical, Inc. (New Castle, Del.), Niro A/S (Soeborg, Denmark), and L. P. Technology, Ltd. (Leeds, England).

Previously, use of an ultrasonic atomizer in combination with a spray-dryer to produce polymeric microparticles has been proposed [12]. However, this approach calls for emulsification of an aqueous drug solution in an organic polymer solution using a high-speed homogenizer and requires thorough mixing of polymer and drug solutions prior to atomization. Moreover, the present invention allows separate processing of two liquids for which prolonged contact can cause undesirable reactions, such as inactivation of protein. By separating the two liquids to the last moment, such adverse reactions can be minimized.

The polymer solvent can also be removed by direct freeze-drying. The polymer solution and the aqueous solution loaded with drugs are atomized using ultrasonic atomizers into a bed of liquefied gas. Microcapsules formed in air as a result of collision among the drops are directly frozen in the liquefied gas. The frozen microcapsules are then transferred to a pre-cooled chamber connected to a freeze-dryer. The solvent is removed by lyophilization. This method is especially advantageous when the active ingredient is sensitive to a high temperature.

Collecting microparticles in liquid nitrogen has been previously proposed by U.S. Pat. No. 5,019,400, issued to Gombotz et al. [8]. Briefly, biodegradable polymer is dissolved in methylene chloride together with a protein powder, and then atomized over a bed of frozen ethanol overlaid with liquid nitrogen. The microdrops freeze upon contacting the liquid nitrogen, and then sink onto the frozen ethanol layer. As the ethanol layer thaws, the frozen microspheres sink into the ethanol. The methylene chloride thaws and is slowly extracted into ethanol, resulting in hardened microspheres containing proteins and polymer matrix. Even though both methods employ liquefied gas to freeze nascent microparticles, this method is readily distinguished because it requires a complete mixture of polymer and the active ingredient prior to atomization and the organic solvent is primarily removed by extraction to the non-solvent.

Removal of solvents by direct lyophilization has been proposed previously by U.S. Pat. No. 6,020,004, issued to Shah [40]. In this method, the solvents are removed by directly lyophilizing emulsions of drug-polymer mixtures in the presence of lyophilization excipients. This is, in essence, a variation of the conventional emulsion method, which involves dissolving or dispersing a drug in a polymer solution and dispersing the drug-polymer mixture in a continuous phase. The uniqueness of this approach lies in the way to remove the organic solvent. Instead of leaving the final emulsion in a continuous phase and causing extraction or evaporation of the solvent, it attempts to lyophilize the resulting emulsion directly to remove the water and organic solvents to form microparticles. However, this method is distinguished by requiring a homogeneous mixture of drug and polymer solutions and by employing emulsification of the two solvents in a continuous phase.

7. Ratio of Flow Rates of Two Solutions ($Q_{Pol}/Q_{Aq}$)

The ratio of flow rates of two solutions plays a significant role in determining the probability of collision between microdrops of two liquids. When the flow rate of the polymer solution ($Q_{Pol}$) is significantly higher than the flow rate of the aqueous solution ($Q_{Aq}$), it is likely that the aqueous drops can easily find the polymer partner. The collision between drops of the two different liquids is followed by spreading of the polymer drops. On the other hand, when $Q_{Pol}$ is not high enough, chances are that aqueous drops will find the other aqueous drops to coalesce into bigger ones.

To visualize the dependence of the collision pattern on the ratio $Q_{Pol}/Q_{Aq}$, embryonic microcapsules forming in air using a coaxial ultrasonic atomizer were captured on a glass plate (Example 8). The aqueous and the polymer solutions were stained with FITC-dextran and Nile Red, respectively, and the captured drops were imaged using a fluorescence microscope. It was observed that when $Q_{Pol}$ is significantly higher than $Q_{Aq}$, the aqueous drop is surrounded by the polymer drops. Concentric circles indicated that coalescence of two drops occurred in air to produce mononuclear microcapsules immediately upon their collision. The hydrodynamic fates of the two liquids were determined by the surface tensions of the liquids. The drops of polymer solution preferentially deformed and surrounded the aqueous drops, while the aqueous drops that had a relatively higher surface tension as compared to that of the organic solvent resisted deformation and were encapsulated within the polymer drops. Preferably, the ratio of $Q_{Pol}/Q_{Aq}$ is in the range of about 1 to about 10.

On the other hand, when $Q_{Pol}$ is lowered to ⅓ of the original flow rate, reversed capsules emerge. When $Q_{Pol}$ was reduced, the polymer drops were exposed to a relatively larger number of aqueous drops. Aqueous drops, which had considerably high surface tension, tended to coalesce with other aqueous drops to form bigger ones. Polymer drops present within the aqueous drops are believed to be those entrapped during the coalescence between aqueous drops.

The dependence of capsule morphology on $Q_{Pol}/Q_{Aq}$ ratio is also observed. When $Q_{Aq}$ was varied from 0.1 to 0.75 ml/min at a fixed level of $Q_{Pol}$ (3 ml/min), the size of the aqueous core decreased and the thickness of the polymer coating increased with a decrease of $Q_{Aq}$.

In summary, the ratio of $Q_{Pol}$ to $Q_{Aq}$ should be balanced in order not only to cause facile collision of the aqueous drops with the polymer drops but also to control thickness of the membrane. It is preferable that $Q_{Pol}$ is higher than $Q_{Aq}$ for maximum probability of collision between drops of two different liquids. A higher ratio of $Q_{Pol}$ to $Q_{Aq}$ can produce a thicker membrane. Optimum microcapsules are obtained using a coaxial atomizer when $Q_{Pol}/Q_{Aq}$ ranges from 1.5/0.25 to 3/0.25. For separated atomizers, the $Q_{Pol}/Q_{Aq}$ ratio need not be so constrained and ratios of 1/1 to 10/1 are acceptable.

8. Absolute Flow Rates

For preferred microencapsulation, both extremes of the flow rates should be avoided. When the flow rates are too low, the population density of the microdrops is not high enough for microdrops to have an opportunity to collide with the other drops. On the other hand, if the flow rates exceed a certain limit, the size distribution tends to shift to a higher value. It is known that the size of particles produced by the ultrasonic atomizer is predicted as [22]:

$$d_{N,0.5}=0.34(8\pi s/\rho f^2)^{1/3}$$

in which s is the surface tension of the liquid, $\rho$ is the density, f is the frequency of vibration. Theoretically, the size distribution is not affected by the flow rate; however, it has been shown to be more or less dependent on the flow rate. At the low end of an atomizer's flow rate range, there is a good correlation between theory and experimental results. On the other hand, as the flow rate reaches the high side of the atomizer's capacity, the particle size tends to grow, which is because there is a tendency for drops in close proximity to each other to coalesce into larger drops. This is the very reason that the ultrasonic system can be adapted for the solvent exchange method. However, an extremely high degree of coalescence is not desirable, because it forms large microcapsules unsuitable for injection. Besides, when the flow rate of the liquid is extremely high, the liquid stream becomes detached from the atomizing surface before it can be atomized, emerging as unatomized stream ("tea pot effect") [22]. In the present application, particle size is influenced by the higher flow rate (i.e., major flow) between the two liquids. Microcapsules of reasonable sizes are obtained when the major flow, which is typically $Q_{Pol}$, is 1.5~3.0 ml/min with the ultrasonic atomizer working at 60 kHz.

9. Volume Ratio of Polymer Solution to Bath

When microcapsules are collected in the bath, the size of the collection bath in relation to the amount of the organic solvent participating in the microencapsulation plays an important role in determining the efficiency of encapsulation. The solvent exchange method is based on an instantaneous mass transfer (solvent exchange) between the solvent and water, which decreases the ability of the solvent to dissolve polymer causing precipitation of the polymer. When the amount of the organic solvent added to the bath exceeds the saturation solubility of the organic solvent in water, the excess solvent tends to separate from water instead of being exchanged with water. In order to ensure effective solvent exchange, the concentration of organic solvent in the proximity of the microcapsules in the bath should be maintained as low as possible: at least lower than the saturation solubility of the solvent in water. Therefore, it is preferable to use a large volume of collection bath to make a sink condition around the solvent exchange area.

For example, the saturation solubility of ethyl acetate in water is 8% w/w. When a total 9 ml (=8 g) of ethyl acetate participates in the microencapsulation, it is preferable to collect the microcapsules in more than 100 ml (=100 g) of water. When the bath size is small to such an extent that the solvent concentration exceeds the saturation solubility, diffusion of the solvent and subsequent solidification of the polymer membrane is significantly delayed. As a result, the polymer drops associated with the aqueous core are gradually detached to form a separate phase instead of leaving a polymer membrane on the core.

10. Formation of Microbubbles

Polymeric microcapsules filled with gas (i.e. microbubbles) can be produced using ultrasonic atomizers immersed in the aqueous bath. Microbubbles are in clinical use as ultrasound contrast agents for sonographic applications [41]. Microbubbles create an acoustic impedance mismatch from biological tissues and fluids, and thus efficiently reflect ultrasound. Recently, microbubbles have been used for local drug delivery and especially for targeted gene delivery [42]. Drugs can be incorporated into the membrane of the microbubbles or internalized into the gas-filled interior of the microbubbles and are released when ultrasound energy ruptures the microbubbles.

Cavitation refers to the formation and subsequent dynamic life of bubbles in liquids. It can be hydrodynamic, thermal, or acoustic in origin and can occur in a variety of liquids under a wide range of conditions [43]. In particular, acoustic cavitation caused by ultrasonic irradiation is an important source of a number of sonochemical phenomena [44]. Sound is transmitted through liquids as a wave consisting of alternating compression and rarefaction cycles. When the rarefaction wave is sufficiently powerful, it can develop a negative pressure large enough to overcome the intermolecular forces present in the liquid. In this situation the molecules can be separated from each other to form tiny bubbles in the medium. The bubbles can originate from density fluctuations of a pure liquid at a given pressure and temperature (i.e., homogeneous nucleation) or foreign substances that stabilize pockets of gas, which become 'nuclei' for the bubble growth (i.e., heterogeneous nucleation).

Microbubbles can be produced by stabilizing the transient gas bubbles, which otherwise will be collapsed by the compression cycle following the rarefaction cycle. Previously, ultrasonic energy has been used to stabilize the gas-liquid interface by cross-linked proteins [45]. A protein solution was ultrasonically irradiated in the presence of oxygen to cause acoustic cavitation. In this example, the acoustic cavitation played dual functions: dispersion of gas into the protein solution and generation of oxidative radicals such as H. and OH. in water, which oxidized free cysteine residues present in the protein. The gas bubbles dispersed in the protein solution were fixed by cross-linking of the cysteine residues of the surrounding proteins and forming proteinaceous microbubbles.

In the present invention, polymeric microbubbles are produced by dispersing a solution of water-insoluble polymer, such as PLGA, in an aqueous bath using an ultrasonic atomizer. Unlike other applications previously described, the ultrasonic atomizer is immersed within the aqueous bath. The function of the ultrasonic atomizer is not only to deliver and atomize the polymer solution to the liquid bath but also to provide ultrasonic irradiation into the bath. Gas bubbles occur in the aqueous bath as the liquid is ultrasonically irradiated. Simultaneously, the bubbles are stabilized by polymer precipitate formed as a result of solvent exchange between the polymer solution and the aqueous bath. The end product is a suspension of hollow polymeric microbubbles less than about 10 $\mu$m in diameter.

Confocal microscopic images clearly visualize that the microbubbles have a polymeric membrane surrounding an air-filled core. When the aqueous bath and polymer solution are labeled with FITC and Nile Red, respectively, the dark appearance of the bubble interior indicates that the core does not contain bath materials. The Nile Red signals show that the polymer phase is a single layer surrounding the gas core.

In a preliminary study, it was shown that an emulsifying agent (PVA) included in the bath plays an important role in formation of microbubbles. When PVA is not included in the bath, a dramatic decrease in microbubble formation was observed. PVA may stabilize the gas bubbles primarily, preventing them from dissolving and allowing deposition of the polymer membrane on their surface, or it may function as a solid inhomogeneity containing gas pockets, which become nuclei of bubble growth upon ultrasonic irradiation.

One of the advantages of this approach is the enhanced stability of the microbubbles. The major drawbacks of commercial ultrasound contrast agents are short plasma half-life and its acoustic instability relative to pressure changes [45]. Unlike commercial products, which are mostly lipid or protein based, the polymeric microbubbles described above are able to withstand acoustic pressure. Moreover, the present method does not require specific properties of the encapsulating materials other than solubility in water. As long as the only requirement that the polymer is insoluble in the bath and thus forms precipitate at the interface between the polymer solution and the bath is satisfied, the polymers can be utilized to make microbubbles. When the microbubbles are used for drug delivery, the use of a separate polymer solution can become another advantage since the drugs can be easily loaded onto the polymer membrane simply by dissolving or suspending them in the polymer solution.

Similarly, polymeric microcapsules filled with non-aqueous liquids can be produced using ultrasonic atomizers submerged in the aqueous bath. In the present invention, non-aqueous microcapsules are produced by extruding a solution of water-insoluble polymer, such as PLGA, and water-insoluble liquids, such as n-dodecane, n-decane, n-hexane, cyclohexane, and toluene, into an aqueous bath using a coaxial ultrasonic atomizer. Hydrophobic drugs can be loaded as a solution in the non-aqueous liquid. Unlike previous examples that produce microcapsules in air, this method can be used to encapsulate hydrophobic drugs.

11. Advantages of the Invention

The present solvent exchange method is a single-step process and thus is much simpler than any other existing microencapsulation techniques. The production scale can be easily modified without affecting the quality of the final products. In addition, the simplicity of the procedure will significantly bring down the overall cost of microcapsule production.

From the mild condition of the encapsulation process and the unique geometry of the microcapsules, the method affords a good opportunity for encapsulation of proteins or peptides. First, conventional methods often include a harsh condition such as an emulsification step, which can exert unfavorable influences on the stability of encapsulated proteins by exposing them to the w/o interface and intensive physical stress. On the other hand, ultrasonic atomization is mild enough to preserve the bioactivity of the drugs. Typically, ultrasonic atomizers utilize very low energy. Even if the mild stress would become a problem, although unlikely, the time the drug is exposed to the ultrasonic vibration is only a fraction of a second. Second, in the mononuclear microcapsules produced by the solvent exchange method, undesirable interactions between drug and the organic solvent or the polymer matrix are limited only to the surface of the core, if any, and do not affect the majority of the drugs.

In solvent exchange methods, the solvent for polymers can be chosen with more flexibility. The double emulsion-solvent extraction/evaporation method requires the organic solvent to be hydrophobic so that it can form an emulsion in water. At the same time, the solvent cannot be too hydrophobic because if the emulsion drops do not stay too long in a liquid state, a significant loss of drugs will be lost into the continuous phase [36]. Therefore, the solvents that can be successfully used in the double emulsion methods are limited to only a few solvents: practically to methylene chloride. This is one of the disadvantages of this method, since methylene chloride is a possible carcinogen and its residual amount should be tightly controlled to meet the regulation.

In contrast, the solvent exchange method can easily overcome these limitations. First, the high water solubility of solvents is not a problem since the solvent exchange method does not depend on formation of an emulsion. Second, the low water solubility of solvents is also not a limiting condition, because the absolute amount of the organic solvent to be removed from individual microcapsules is less than for those produced by the emulsion method. In the solvent exchange method, solidification of the polymer membrane occurs quickly before the drug is lost. Furthermore, encapsulation efficiency can be significantly improved in the solvent exchange method. Drug loss across the dispersed drop interfaces occurs only during the first minutes before polymer precipitates [36]. When the microparticle is sealed as the polymer solidifies, diffusion of the drug into the continuous phase is limited. In the solvent exchange method, the precipitation occurs quickly, not only because the preferred solvent is hydrophilic, but also because the absolute amount of solvent to be removed is small. As shown in Example 10, the encapsulation efficiency of this encapsulation method is as high as 80% on average. Depending on the formulation variables, the encapsulation efficiency can reach near 100%.

Finally, the solvent exchange method can be used not only as a microencapsulation technique, but also as a means to coat stents with a mixture of a polymer and a water-soluble drug. Drug coated stents are becoming an increasing popular approach for the controlled delivery of drugs. Microcapsules produced in air can be captured on the stent surface to form one or multiple layers of coating. The use of ultrasonic atomizers is particularly advantageous for this application because of the unique capability of the device to produce a low-velocity spray that eliminates overspray problems.

The following examples are offered to illustrate the present invention and do not limit it. The embodiments shown are for illustration only, inasmuch as obvious variations will become obvious to those skilled in the art.

EXAMPLE 1

Microencapsulation Using a Coaxial Ultrasonic Atomizer ($Q_{out}/Q_{in}=Q_{Pol}/Q_{Aq}$).

A solution of 2% PLGA in ethyl acetate and an aqueous solution containing 0.2% sodium alginate were delivered into a coaxial ultrasonic atomizer using syringe pumps at controlled flow rates. FIG. 1. The aqueous solution flowed through the inner nozzle at 0.25 ml/min and the polymer solution flowed through the outer nozzle at 1.5 ml/min. Optionally, 0.02% Coomassie Blue was added to the aqueous solution for visualization of microcapsules using a bright field microscope. For confocal microscopy, the dye in the aqueous solution was replaced with 2.8 mg/ml FITC-dextran, and 0.4 mg/ml Nile Red was added to ethyl acetate. Upon the onset of the ultrasonic vibration of the atomizer, both liquids were fragmented into microdrops. The collision of multiple drops in air produced microcapsules. Thus formed microcapsules were collected in a water bath containing 0.15 M calcium chloride for stabilization of the microcapsules through formation of calcium-alginate gel. The size distribution of the microcapsules was determined using a Microtrac Full Range Particle Size Analyzer 9200. The microcapsules were imaged using a bright field microscope (Panels A,B) and a confocal or scanning electron microscope (Panel C) as shown in FIG. 2.

For comparison, microspheres were also produced using a double emulsion-solvent evaporation method described in the literature [37] with a slight modification. 50 µl of aqueous FITC-dextran solution (20%) was poured into 1 ml of methylene chloride containing 33% PLGA and 0.003% Nile Red. The solution was mixed for 1 min using a vortex mixer. The resulting w/o emulsion was poured under magnetic stirring into 2 ml of aqueous 1% PVA solution saturated with methylene chloride to form a w/o/w emulsion. The w/o/w double emulsion was poured into 200 ml of water containing 0.1% PVA and continuously stirred for 3 hours at room temperature until most of methylene chloride evaporated, leaving solid microspheres. The formed microcapsules were imaged using a confocal microscope.

FIG. 9 illustrates bright field microscopic pictures of microcapsules produced with an ultrasonic atomizer using 2% PLGA solution in ethyl acetate and various combinations of aqueous solution and collection bath following the procedure set forth above. Scale bar: 100 µm (A); 50 µm (B, C, and D)

| Panel | Aqueous solution | Collection bath |
| --- | --- | --- |
| A | 1% Na CMC + 0.05% amaranth | 5% FeCl$_3$ + 1% PVA |
| B | 2.5% Na CMC + 0.05% amaranth | 5% Al(NO$_3$)$_3$ + 1% PVA |
| C | 0.25% Pectin | 0.5 M CaCl$_2$ + 1% PVA |
| D | 0.2% κ-Carrageenan | 0.5 M KCl + 1% PVA |

EXAMPLE 2
Microencapsulation Using a Coaxial Ultrasonic Atomizer ($Q_{out}/Q_{in}=Q_{Aq}/Q_{Pol}$).

A solution of 2% PLGA in ethyl acetate and an aqueous solution containing 0.2% sodium alginate were delivered into a coaxial ultrasonic atomizer using syringe pumps at controlled flow rates as shown in FIG. 3 (Panel A). The polymer solution flowed through the inner nozzle at 1.5 ml/min and the aqueous solution flowed through the outer nozzle at 0.25 ml/min. Optionally, 0.02% Coomassie Blue was added to the aqueous solution for visualization by light microscopy. Upon the onset of the ultrasonic vibration of the atomizer, both liquids were fragmented into microdrops. The collision of multiple drops in air produced microcapsules. Thus formed microcapsules were collected as described in Example 1.

EXAMPLE 3
Microencapsulation Using an Ultrasonic Atomizer Without a Coaxial Cable.

A solution of 2% PLGA in ethyl acetate and an aqueous solution containing 0.2% sodium alginate were delivered into an ultrasonic atomizer, through separate inlets. The polymer solution flowed at 1.5 ml/min and the aqueous solution flowed at 0.25 ml/min. Upon the onset of ultrasonic vibration of the atomizer, both liquids were fragmented into microdrops. The collision of multiple drops in air produced microcapsules. Thus formed microcapsules were collected as described in Example 1.

EXAMPLE 4
Microencapsulation Using Separate Ultrasonic Atomizers.

A solution of 2% PLGA in ethyl acetate and an aqueous solution containing 0.2% sodium alginate were delivered into two ultrasonic atomizers respectively using syringe pumps at controlled flow rates. The polymer solution flowed through one atomizer at 1.5 ml/min and the aqueous solution flowed through the other atomizer at 0.25 ml/min. Optionally, 0.02% Coomassie Blue was added to the aqueous solution for visualization by light microscopy. Upon the onset of the ultrasonic vibration of the atomizers, both liquids were fragmented into microdrops. Two atomizers were aligned so that two liquid sprays could be coincided as shown in FIG. 3 (Panel B). The collision of multiple drops in air produced microcapsules. The microcapsules formed were collected as described in Example 1.

EXAMPLE 5
Microencapsulation Using Coaxial Ultrasonic Atomizer Submerged in Collection Bath.

Microcapsules can be produced by submerging the atomizer in a collection bath and inducing solvent exchange by contact of the polymer solution and the collection bath as shown in FIG. 3 (Panel D). 2% PLGA solution in ethyl acetate was fed into an ultrasonic atomizer at the flow rate=1.5 ml/min using a syringe pump. For observation by confocal microscopy, 0.4 mg/ml Nile Red was added to the polymer solution. The atomizer was submerged in the collection bath consisting of water. As the vibration frequency was imposed on the atomizer at 60 kHz, the PLGA solution delivered via the ultrasonic atomizer was fragmented into microcapsules ranging 5~100 µm in diameter. When the microparticles were visualized by confocal microscope, they were observed to be hollow microcapsules.

EXAMPLE 6
Particle Size Reduction Using Extra Piezoelectric Device.

The particle size can be reduced after microencapsulation by secondary fragmentation of the embryonic microcapsules. A piezoelectric device vibrating at a high frequency was placed underneath the atomizer (FIG. 4). The emerging microcapsules were broken into smaller particles upon hitting the vibrating piezoelectric device. Thus formed microcapsules were collected as described in Example 1.

EXAMPLE 7
Stent Coating.

The solvent exchange method can be used as a means to deposit polymer coating containing water-soluble drugs on stents. The microcapsules produced by the method described in Example 1 are deposited on the stents. The solvent can be removed by evaporation. In order to facilitate the evaporation, the path that microcapsules fly in air can be extended and/or mild heat can be applied to the flying microcapsules. The layer of microcapsules thus formed on the stent contains aqueous cores including drug substances, and the polymer that controls the drug release rate.

For a feasibility check, the microcapsules were captured on a glass plate and observed by microscope. A solution of 2% PLGA in ethyl acetate labeled with 0.4 mg/ml Nile Red and an aqueous solution containing 0.2% sodium alginate and 2.8 mg/ml FITC-dextran were delivered into a coaxial ultrasonic atomizer using syringe pumps at controlled flow rates. The aqueous solution flowed through the inner nozzle at 0.25 ml/min and the polymer solution flowed through the outer nozzle at 1.5 ml/min. Upon the onset of ultrasonic vibration of the atomizer, both liquids were fragmented into microdrops. The microdrops were captured on the glass plate by quickly passing the plate under the atomizer so that only one layer of spray could be deposited. Captured microdrops were observed using a fluorescence microscope with polymer drops appearing red due to the presence of fluorescence dye Nile Red and the aqueous drops appearing green due to FITC-dextran.

EXAMPLE 8

Dependence of the Collision Pattern on the Ratio $Q_{Pol}/Q_{Aq}$.

In order to prove that the microcapsules are products of coalescence of two drops in air, the microcapsules were captured on a glass plate and observed by microscope. A solution of 2% PLGA in ethyl acetate labeled with 0.4 mg/ml Nile Red and an aqueous solution containing 0.2% sodium alginate and 2.8 mg/ml FITC-dextran were delivered into a coaxial ultrasonic atomizer using syringe pumps at controlled flow rates. The aqueous solution flowed through the inner nozzle at 0.25 ml/min and the polymer solution flowed through the outer nozzle at 1.5 or 0.5 ml/min. Upon the onset of the ultrasonic vibration of the atomizer, both liquids were fragmented into microdrops. The microdrops were captured on the glass plate by quickly passing the plate under the atomizer so that only one layer of spray could be deposited. Captured microdrops were observed using a fluorescence microscope.

EXAMPLE 9

Screening of Organic Solvents.

Organic solvents having the Hildebrand solubility parameter of 16~24 $MPa^{1/2}$ were screened for polymer solvency. 125 mg of PLGA was added to glass vials containing 5 ml of solvents. The vials were agitated overnight at room temperature. Solubility of PLGA in a particular solvent was judged by visual examination. Solvents were classified into four groups: good solvents (forming clear polymer solution); intermediately good solvents (forming turbid polymer solution upon heating); intermediately poor solvents (marginally able to swell the PLGA); and poor solvents. The results are summarized on a triangular graph developed by Teas [38], according to Hansen's solubility parameters [39] of the solvents (FIG. 5).

The second and third qualities of the solvent were examined by a simple screening tool called the hydrogel method. A library of PLGA solutions (5% w/v) was constructed using the good solvents selected above. A 10 μl drop of each solution was placed on a layer of hydrogel containing 0.5% agarose. The diameter of the polymer film that formed on the gel was measured 10 seconds after the placement. In order to assess the quality of the polymer membrane, a microplate containing 200 μl of agarose gel in each well was prepared to which 5 μl of each PLGA solution was simultaneously applied. The turbidity of the film developed after 1 minute and was measured at 620 nm using a microplate reader. See FIGS. 6 and 7.

EXAMPLE 10

Determination of Loading and Encapsulation Efficiencies

Loading and encapsulation efficiencies were defined as follows:

Loading efficiency, LE (%)=100×(Encapsulated protein/Microparticle weight)

Theoretical loading efficiency, TLE (%)=100×(Protein used for encapsulation/Microparticle weight)

Encapsulation efficiency, EE (%)=100×(Encapsulated protein/Protein used for encapsulation)=100×LE/TLE For determination of loading and encapsulation efficiencies of the microcapsules: Microcapsules, accurately weighed (<10 mg), were put into a microcentrifuge tube, to which 0.2 ml of dimethyl sulfoxide (DMSO) was added. The microcapsules were dissolved by vortexing. 0.8 ml of NaOH/SDS/Citric acid trisodium salt solution (0.05N/0.5%/0.075M) was then added to the tube and mixed. After sonicating for 90 min at 25° C., samples were centrifuged at 10,000 rpm for 5 min. Aliquots of the clear DMSO/NaOH/SDS/Citrate solution were pipetted into the wells of a microplate. Samples were analyzed using the bicinchoninic acid (BCA) assay method.

For determination of loading and encapsulation efficiencies of the uncoated alginate microparticles: Microparticles, accurately weighed (<3 mg), were put into a microcentrifuge tube, to which 1.0 ml of NaOH/SDS/Citric acid trisodium salt solution (0.05N/0.5%/0.075M) was added. The microparticles were dissolved by vortexing. After sonicating for 90 min at 25° C., samples were centrifuged at 10,000 rpm for 5 min. Aliquots of the clear NaOH/SDS/Citrate solution were pipetted into the wells of a microplate. Samples were analyzed using the BCA assay method. The results are shown in Table 3.

TABLE 3

Loading and encapsulation efficiencies of microcapsules produced by Example 1.

| PLGA solution (%) | Aqueous solution (%) | Collection bath (0.5% PVA+) | TLE (%) | LE (%) | EE (%) |
|---|---|---|---|---|---|
| 5% in EA | 0.7% pectin + 3% BSA | — | 4.70 | 5.20 | 110.4 |
|  |  |  |  | 4.20 | 89.0 |
|  |  |  |  | 4.10 | 86.7 |
| 5% in EA | 0.5% alginate + 3% BSA | — | 4.74 | 3.60 | 77.0 |
|  |  | 0.15 M $CaCl_2$ |  | 3.60 | 76.7 |
| 5% in EA | 0.5% alginate + 3% BSA | 0.15 M $CaCl_2$ 0.75 M $CaCl_2$ | 4.67 | 3.28 2.20 | 70.3 47.0 |
|  |  | 0.15 M Zn acetate |  | 3.36 | 71.8 |
|  | 0.5% PVA + 3% Zn-BSA | — | 4.66 | 3.62 | 77.7 |
| 5% in EA | 0.5% alginate + 3% BSA | 0.15 M $CaCl_2$ 0.75 M $CaCl_2$ | 4.68 | 4.13 2.70 | 88.2 57.6 |
|  |  | 0.15 M Zn acetate 0.75 M Zn acetate |  | 4.82 3.26 | 103.1 69.6 |
| — | 0.5% alginate + 3% BSA | 0.15 M $CaCl_2$ 0.75 M $CaCl_2$ | 85.6 | 2.64 2.11 | 3.1 2.5 |

EXAMPLE 11

Characterization of BSA from Embryonic Microparticles

To dissolve PLGA selectively, 1 ml of DMSO was added to the embryonic microparticles suspended in 100 μl of distilled water (DW). DMSO supernatant containing PLGA was discarded and the protein debris was washed with fresh DMSO three times to remove polymer remnant. Protein debris was collected by centrifugation (6000 rpm, 1 min) and was dissolved in 1 ml of PBS. The protein solution was subjected to non-reducing polyacrylamide gel electrophoresis (PAGE). The gel was stained by the Coomassie Blue method. BSA powder was treated with the same procedure in order to make sure that the above procedure did not bring about any conformational change to the BSA.

EXAMPLE 12

Characterization of BSA from Freeze-dried Microparticles 1 ml of DMSO was added to the dried microparticles to dissolve PLGA selectively. DMSO supernatant containing PLGA was discarded and the protein debris was washed with fresh DMSO three times to remove polymer remnant. Protein debris was collected by centrifugation (6000 rpm, 1 min), and was dissolved in 1 ml of PBS. The protein solution was subjected to non-reducing PAGE. The gel was stained by the Coomassie Blue method. BSA powder was treated with the same procedure in order to make sure that the above procedure did not bring about any conformational change to the BSA.

EXAMPLE 13
Characterization of Unreleased BSA from Microparticles

Remaining microcapsules were collected by centrifugation at 10000 rpm for 3 min and washed with DW three times to remove BSA present in the outside of the microcapsules. Microcapsules were frozen at −20° C. and freeze-dried overnight. 1 ml of DMSO was added to the dried microcapsules to dissolve PLGA selectively. DMSO supernatant containing PLGA was discarded and the protein debris was washed with fresh DMSO three times to remove polymer remnant. Protein debris was collected by centrifugation (6000 rpm, 1 min), and was dissolved in 1 ml of PBS. The protein solution was subjected to non-reducing PAGE. The gel was stained by the Coomassie Blue method. BSA powder was treated with the same procedure in order to make sure that the above procedure did not bring about any conformational change to the BSA.

EXAMPLE 14
Characterization of Lysozyme from Embryonic Microparticles

300 µl of DMSO was added to the embryonic microparticles suspended in 100 µl of DW to dissolve both lysozyme and PLGA. After the microparticles were completely dissolved, 700 µl of DW was added to the solution. The resulting suspension was centrifuged at 6000 rpm for 1 min. Proteins in the supernatant were subjected to non-reducing PAGE. The gel was stained by the Coomassie Blue method. 100 µl of 10 mg/ml lysozyme solution was treated with the same procedure in order to make sure that the above procedure did not bring about any conformation change to the lysozyme.

EXAMPLE 15
Characterization of Lysozyme from Freeze-dried Microparticles

300 µl of DMSO was added to the dried microparticles to dissolve both lysozyme and PLGA. After the microparticles were completely dissolved, 700 µl of DW was added to the solution. Resulting suspension was centrifuged at 6000 rpm for 1 min. Proteins in the supernatant were subjected to non-reducing PAGE. The gel was stained by the Coomassie Blue method. 100 µl of 10 mg/ml lysozyme solution was treated by the same procedure in order to ensure that the method did not bring about any conformation change to the lysozyme.

EXAMPLE 16
Characterization of Unreleased Lysozyme from Microparticles

The remaining microcapsules were collected by centrifugation at 10000 rpm for 3 min and washed with DW three times to remove lysozyme present in the outside of the microcapsules. Microcapsules were frozen at −20° C. and freeze-dried for overnight. 300 µl of DMSO was added to the dried microparticles to dissolve both lysozyme and PLGA. After the microparticles were completely dissolved, 700 µl of DW was added to the solution. Resulting suspension was centrifuged at 6000 rpm for 1 min. Proteins in the supernatant were subjected to non-reducing PAGE. The gel was stained by the Coomassie Blue method. Lysozyme powder was subjected to the same procedure in order to make sure that the above procedure did not bring about any conformational change to the lysozyme.

EXAMPLE 17
Formation of Microbubbles Using Ultrasonic Atomizer Submerged in Bath.

Microbubbles can be produced by submerging the atomizer in a water bath and inducing solvent exchange from contact of the polymer solution and the collection bath. 2% PLGA solution in ethyl acetate was fed into an ultrasonic atomizer at the flow rate=1.5 ml/min using a syringe pump. For observation by confocal microscopy, 0.4 mg/ml Nile Red was added to the polymer solution. The atomizer was submerged in the collection bath consisting of water and 0.5% PVA. In order to visualize the air entrapped within the microbubble, the bath was labeled with FITC. As the vibration frequency was imposed on the atomizer at 60 kHz, the PLGA solution delivered via the ultrasonic atomizer was fragmented into microbubbles in the range of about 5 to 100 µm in diameter. Confocal microscopic images of the microbubbles show the cores appearing dark, indicating that they did not contain either bath materials or polymer but were filled with air.

EXAMPLE 18
Formation of Microcapsules Filled with Non-aqueous Liquids Using a Coaxial Ultrasonic Atomizer Submerged in the Bath.

Microcapsules filled with non-aqueous liquids can be produced by submerging a coaxial ultrasonic atomizer in the bath and extruding a solution of water-insoluble polymer such as PLGA and water-insoluble liquids. A solution of 2% PLGA in ethyl acetate and n-decane were delivered into a coaxial ultrasonic atomizer using syringe pumps at controlled flow rates. The n-decane flowed through the inner nozzle at 0.25 ml/min and the polymer solution flowed through the outer nozzle at 1.5 ml/min. For confocal microscopy, the polymer solution and the non-aqueous liquid (n-decane) were labeled with two lipophilic dyes, Nile Red and DiO (3,3'-dioctadecyloxacarbocyanine perchlorate), respectively, which are commercially available from Sigma Corp. (St. Louis, Mo.). Upon onset of the ultrasonic vibration of the atomizer, both liquids were fragmented into microdrops in the collection bath. Mononuclear microcapsules formed as drops of the two solutions coalesced. It is likely that since the non-aqueous liquids are also non-solvents for the polymer the contact between two drops induced immediate precipitation of polymer at their interfaces through solvent exchange.

Just like for microcapsules forming in air, the solvent exchange occurring at the interface of the two liquids was the driving force to form a membrane around the drop of non-aqueous liquid and cause precipitation of the polymer in the collection bath. Immediately after encapsulation, the microcapsules looked mononuclear, of which a non-aqueous core was surrounded by polymer membrane. Later, the microcapsules appeared homogeneously in orange when observed with confocal microscopy, a combination of red (Nile Red) and green (DiO), most likely because the two lipophilic dyes partitioned into the other phases with time.

EXAMPLE 19
Use of Non-ultrasonic Atomizers

Other types of atomizers other than ultrasonic ones can be used to generate microdroplets that undergo solvent exchange to afford microcapsules according to the principles of the present invention. Even though the above examples are implemented using ultrasonic atomizers as an exemplary atomizer, a variety of atomization techniques can be employed for the same purpose. Different commercial atomizers are categorized in terms of the different types of energy used to break up bulk liquid into drops. Possible examples include rotary atomizers that utilize centrifugal energy, centrifugal atomizers using pressure energy, and pneumatic atomizers utilizing kinetic energy, in addition to the sonic atomizers using sonic energy.

The present invention has been described hereinabove with reference to certain examples for purposes of illustration and explanation. It should be appreciated that certain obvious improvements and modifications can be practiced within the scope of the appended claims.

References

Those references cited hereinabove are listed as follows by footnote number and their pertinent disclosures are incorporated herein by reference.

1. Langer, R. and Folkman, J., 1976. "Polymers for the sustained release of proteins and other macromolecules" Nature, 263: 797–800.
2. Ogawa, Y., Yamamoto, M., Okada, H., Yashiki, T. and Shimamoto, T., 1988. "A new technique to efficiently entrap leuprolide acetate int microcapsules of polylactic acid or copoly(lactic/glycolic) acid" Chem Pharm Bull, 36: 1095–1103.
3. Ogawa, Y., Okada, H., Yamamoto, M. and Shimamoto, T., 1988. "In vivo release profiles of leuprolide acetate from microcapsules prepared with polylactic acids or copoly (lactic/glycolic) acids and in vivo degradation of these polymers" Chem Pharm Bull, 36: 2576–2581.
4. Vrancken, M. N. and Claeys, D. A., 1970. Process for encapsulating water and compounds in aqueous phase by evapration. U.S. Pat. No. 3,523,906.
5. Tice, T. R. and Lewis, D. H., 1983. Microencapsulation process. U.S. Pat. No. 4,389,330.
6. van de Weert, M., Hennink, W. E. and Jiskoot, W., 2000. "Protein instability in PLGA microparticles" Pharm Res, 17: 1159–1167.
7. Gombotz, W. R., et al., 1991. Very low temperature casting of controlled release microspheres. U.S. Pat. No. 5,019,400.
8. Knutson, B. L., Debenedetti, P. G. and Tom, J. W., 1996. "Preparation of microparticulates using supercritical fluids" In: Cohen, S. and Bernstein, H. (Eds.), Microparticulate Systems for the Delivery of Proteins and Vaccines. Marcel Dekker, Inc., New York, USA, pp. 89–125.
9. Mumenthaler, M., Hsu, C. C. and Pearlman, R., 1994. "Feasibility study on spray-drying protein pharmaceuticals: rhGH and t-PA" Pharm Res, 11: 12–20.
10. Maa, Y.-F., Nguyen, P.-A. T. and Hsu, S. W., 1998. "Spray-drying of air-liquid interface sensitive recombinant human growth hormone" J Pharm Sci, 87: 152–159.
11. Rodriguez, L., Passerini, N., Cavallari, C., Cini, M., Sancin, P. and Fini, A., 1999. "Description and preliminary evaluation of a new ultrasonic atomizer for spray-congealing processes" Int J Pharm, 183: 133–143.
12. Bittner, B. and Kissel, T., 1999. "Ultrasonic atomization for spray drying: a versatile technique for the preparation of protein loaded biodegradable microspheres" J Microencapsulation, 16: 325–341.
13. Dirix, C. A. M. C., et al., 1995. Process for the preparation of biologically active material containing polymeric microcapsules. U.S. Pat. No. 5,389,379.
14. Thies, C., 1996. "A survey of microencapsulation processes" In: Benita, S. (Ed.), Microencapsulation: Methods and Industrial Applications. Marcel Dekker, Inc., New York, USA, pp. 1–19.
15. Benoit, J.-P., Marchais, H., Rolland, H. and Velde, V. V., 1996. "Biodegradable microspheres: Advances in production technology" In: Benita, S. (Ed.), Microencapsulation: Methods and Industrial Application. Marcel Dekker, Inc., New York, USA, pp. 35–72.
16. Zhu, G., Mallery, S. R. and Schwendeman, S. P., 2000. "Stabilization of proteins encapsulated in injectable PLGA" Nat Biotechnol, 18: 52–57.
17. Kim, H. K. and Park, T. G., 1999. "Microencapsulation of human growth hormone within biodegradable polyester microspheres: protein aggregation stability and incomplete release mechanism" Biotechnol Bioeng, 65: 659–667.
18. Gustavsson, N. O., et al., 2002. Microparticles. Patent Publication US 20020044976 A1.
19. Reslow, M., Gustafsson, N.-O., Jonsson, M. and Laakso, T., 2002. "Polymer coated starch microspheres as protein delivery system" 29th International Symposium on Controlled Release of Bioactive Materials, Seoul, Korea, pp. #698.
20. Yeo, Y., et al., 2002. Microencapsulation of drugs by solvent exchange. Patent Publication US 2002/0160109 A1.
21. Yeo, Y., Chen, A. U., Basaran, O. A. and Park, K., 2002. "Solvent exchange method: A novel microencapsulation technique" 29th International Symposium on Controlled Release of Bioactive Materials, Seoul, Korea, pp. 547–548.
22. Berger, H. L., 1998. Ultrasonic liquid atomization. Partridge Hill Publishers.
23. Sono-Tek, 2002. Technology overview (Sono-Tek ultrasonic nozzle).
24. Wise, D. L., Trantolo, D. J., Altobelli, D. E., Yaszemski, M. J., Gresser, J. D. and Schwartz, E. R., 1995. Encyclopedic handbook of biomaterials and bioengineering. Marcel Dekker, Inc. New York.
25. Wypych, G., 2000. Solvents Database. ChemTec Publishing.
26. Barton, A. F. M., 1975. Solubility parameters. Chemical Reviews, 75: 731–753.
27. Sah, H., 1997. "Microencapsulation techniques using ethyl acetate as a dispersed solvent: effects of its extraction rate on the characteristics of PLGA microspheres" J Controlled Release, 47: 233–245.
28. Sah, H., 1999. "Protein instability toward organic solvent/water emulsification: implications for protein microencapsulation into microspheres" PDA J Pharm Sci Technol, 53: 3–10.
29. Sturesson, C. and Carlfors, J., 2000. "Incorporation of protein in PLG microspheres with retention of bioactivity" J Controlled Release, 67: 171–178.
30. Soppimath, K. S., Kulkarni, A. R. and Aminabhavi, T. M., 2001. "Encapsulation of antihypertensive drugs in cellulose-based matrix microspheres: characterization and release kinetics of microspheres and tableted microspheres" J Microencapsulation, 18: 397–409.
31. Sah, H., Smith, M. and Chern, R., 1996. "A novel method of preparing PLGA microcapsules utillizing methylethyl ketone" Pharm Res, 13: 360–367.
32. Yeo, Y., Back, N. and Park, K., 2001. "Microencapsulation methods for delivery of protein drugs" Biotechnol Bioprocess Eng, 6: 213–230.
33. Kibbe, A. H., 2000. Handbook of pharmaceutical excipients, 3rd ed. American Pharmaceutical Association Pharmaceutical press. Washington, D.C.; London, UK.

34. Edsman, K., Carlfors, J. and Petersson, R., 1998. "Rheological evaluation of poloxamer as an in situ gel for ophthalmic use. European journal of pharmaceutics and biopharmaceutics", 6: 105–112.
35. Jeong, B., Kim, S. W. and Bae, Y. H., 2002. "Thermosensitive sol-gel reversible hydrogels" Advanced Drug Delivery Reviews, 54: 37–51.
36. Bodmeier, R. and McGinity, J. W., 1988. "Solvent selection in the preparation of PLA microspheres prepared by the solvent evaporation method" Int J Pharm, 43: 179–186.
37. Cohen, S., Yoshioka, T., Lucarelli, M., Hwang, L. H. and Langer, R., 1991. "Controlled delivery systems for proteins based on PLGA microspheres" Pharm Res, 8: 713–720.
38. Teas, J. P., 1968. "Graphic analysis of resin solubilities" J. Paint Technol., 40: 19–25.
39. Hansen, C. M., 1967. "The three dimensional solubility parameter—Key to paint component affinities: II and III" J. Paint Technol., 39: 505–514.
40. Shah, S. Biodegradable microparticles for the sustained delivery of therapeutic drugs. U.S. Pat. No. 6,020,004.
41. Grinstaff, M. W. and Suslick, K. S., 1991. "Air-filled proteinous microbubbles: synthesis of an echo-contrast agent" Proc. Natl. Acad. Sci. USA, 88: 7708–7710.
42. Unger, E. C., Hersh, E., Vannan, M., Matsunaga, T. O. and McCreery, T., 2001. "Local drug and gene delivery through microbubbles" Progress in Cardiovascular Diseases, 44: 45–54.
43. Suslick, K. S., 1988. Ultrasound: Its chemical, physical, and biological effects.
44. Mason, T. J., 1990. Chemistry with ultrasound.
45. Watkin, K. L. and McDonald, M. A., 2002. "Multi-modal contrast agents: A first step" Academic Radiology, 9: S285–S289.

What is claimed is:

1. A method for preparing a microencapsulated composition, comprising:
    providing an aqueous solution containing a composition to be encapsulated dissolved therein;
    providing a polymer solution containing a water-insoluble polymer dissolved in a hydrophilic solvent;
    generating a plurality of first microdroplets from the aqueous solution;
    generating a plurality of second microdroplets from the polymer solution, wherein the first and second microdroplets are generated by at least one ultrasonic atomizer; and
    contacting the first and second microdroplets to form a plurality of pre-encapsulant particles, which have a core domain containing said composition and an outer layer containing said polymer, such that solvent exchange occurs between the core domain and the outer layer so as to afford a plurality of microcapsules containing said composition.

2. The method of claim 1, wherein the encapsulated composition is a physiologically active substance.

3. The method of claim 2, wherein the encapsulated composition is a low molecular weight drug, a protein, an oligonucleotide, a gene, or a polysaccharide.

4. The method of claim 1, wherein a coaxial ultrasonic atomizer is employed to generate the first and second microdroplets.

5. The method of claim 4, wherein said contacting is conducted underwater.

6. The method of claim 1, wherein separate ultrasonic atomizers are employed to generate the first and second microdroplets, respectively.

7. The method of claim 1, further comprising collecting the microcapsules in a bath containing a nonsolvent for the polymer.

8. The method of claim 7, wherein the bath contains water.

9. The method of claim 7, further comprising freeze-drying of the microcapsules after collection.

10. The method of claim 1, further comprising spray drying of the microcapsules substantially concurrently with microcapsule formation.

11. The method of claim 1, further comprising fragmenting the pre-encapsulant particles with a piezoelectric device.

12. The method of claim 1, wherein the encapsulated composition exhibits controlled release properties.

13. The method of claim 1, wherein the microcapsules have a particle size in the range of about 0.1 to about 500 $\mu$m.

14. The method of claim 1, wherein the water-insoluble polymer is biocompatible.

15. The method of claim 14, wherein the polymer is biodegradable.

16. The method of claim 15, wherein the biodegradable polymer is a homopolymer of lactic acid or glycolic acid or a copolymer of lactic acid and glycolic acid (PLGA).

17. The method of claim 1, wherein the hydrophilic solvent is selected from the group consisting of acetic acid, ethyl acetate, methyl acetate and ethyl formate.

18. The method of claim 1, wherein the hydrophilic solvent has a Hildebrand solubility parameter in the range of 16 to 26 MPa$^{1/2}$.

19. The method of claim 1, wherein the hydrophilic solvent has a surface tension of less than about 45 mN/m.

20. The method of claim 1, wherein the hydrophilic solvent has a water solubility of 5 to 100%.

21. The method of claim 1, wherein the aqueous solution contains a hydrophilic polymer capable of undergoing a sol-to-gel transition.

22. The method of claim 1, wherein the aqueous solution contains a hydrophilic polymer that increases the viscosity of the aqueous solution.

23. The method of claim 1, wherein the aqueous solution is provided with a protective excipient.

24. An encapsulated composition made by the method of claim 1.

25. A method for preparing microbubbles loaded with a hydrophobic substance comprising atomizing underwater a solution containing a water-insoluble polymer and the hydrophobic substance dissolved therein, wherein solvent exchange occurs between the polymer-containing solution and the surrounding water to form a polymer shell around a hollow core.

26. The method of claim 25, wherein the hydrophobic substance is a drug.

27. The method of claim 25, wherein the polymer is a homopolymer of lactic acid or glycolic acid or a copolymer of lactic acid and glycolic acid (PLGA).

28. A method for preparing a microencapsulated hydrophobic composition, comprising:
    providing a non-aqueous liquid containing the hydrophobic composition to be encapsulated dissolved therein;
    providing a polymer solution containing a water-insoluble polymer dissolved in a hydrophilic solvent; and
    generating underwater a plurality of first microdroplets from the non-aqueous liquid concurrently with a plurality of second microdroplets from the polymer solution using a coaxial ultrasonic atomizer, in proximity and under conditions such that solvent exchange occurs between the non-aqueous liquid and the polymer solution and, optionally, between the polymer solution and bath so as to afford a plurality of microcapsules having a polymer shell and a core domain containing the hydrophobic composition.

29. The method of claim 28, wherein the hydrophobic composition is a drug.

30. The method of claim 28, wherein the polymer is a homopolymer of lactic acid or glycolic acid or a copolymer of lactic acid and glycolic acid (PLGA).

* * * * *